United States Patent
van Loevezijn et al.

(10) Patent No.: US 9,422,244 B2
(45) Date of Patent: Aug. 23, 2016

(54) SYNTHESIS OF SUBSTITUTED PYRAZOLINE CARBOXAMIDINE DERIVATIVES

(75) Inventors: Arnold van Loevezijn, Weesp (NL); Josephus H. M. Lange, Weesp (NL); Gerrit A. Barf, Weesp (NL); Arnold P. den Hartog, Weesp (NL)

(73) Assignee: Abbvie Bahamas Ltd., New Providence, Nassau (BS)

( * ) Notice: Subject to any disclaimer, the term of this patent is extended or adjusted under 35 U.S.C. 154(b) by 0 days.

(21) Appl. No.: 13/574,176

(22) PCT Filed: Jan. 27, 2011

(86) PCT No.: PCT/EP2011/051100
§ 371 (c)(1),
(2), (4) Date: Nov. 9, 2012

(87) PCT Pub. No.: WO2011/092226
PCT Pub. Date: Aug. 4, 2011

(65) Prior Publication Data
US 2013/0060041 A1    Mar. 7, 2013

Related U.S. Application Data

(60) Provisional application No. 61/299,363, filed on Jan. 29, 2010.

(30) Foreign Application Priority Data

Jan. 29, 2010 (EP) ..................... 10152097

(51) Int. Cl.
| | | |
|---|---|---|
| *C07D 231/54* | (2006.01) | |
| *C07D 231/06* | (2006.01) | |
| *C07D 409/04* | (2006.01) | |
| *C07D 409/12* | (2006.01) | |
| *C07D 491/107* | (2006.01) | |
| *C07D 513/10* | (2006.01) | |

(52) U.S. Cl.
CPC ............ *C07D 231/06* (2013.01); *C07D 231/54* (2013.01); *C07D 409/04* (2013.01); *C07D 409/12* (2013.01); *C07D 491/107* (2013.01); *C07D 513/10* (2013.01)

(58) Field of Classification Search
CPC .. C07D 231/06; C07D 231/54; C07D 409/04; C07D 409/12; C07D 491/107; C07D 513/10
USPC ........ 548/357.5, 364.4, 365.7, 379.4; 546/20, 546/211
See application file for complete search history.

(56) References Cited

U.S. PATENT DOCUMENTS

| | | | |
|---|---|---|---|
| 4,156,007 A | | 5/1979 | Van Daalen et al. |
| 4,200,641 A | * | 4/1980 | Vandenberk et al. ......... 514/318 |
| 7,728,018 B2 | * | 6/2010 | Van Loevezijn et al. ..... 514/364 |
| 8,563,723 B2 | * | 10/2013 | Van Loevezijn et al. ....... 546/20 |
| 2007/0142362 A1 | * | 6/2007 | Lange et al. ............. 514/217.09 |
| 2009/0163545 A1 | | 6/2009 | Goldfarb |

FOREIGN PATENT DOCUMENTS

| | | |
|---|---|---|
| CN | 101341127 A | 1/2009 |
| JP | 60-8211 A | 1/1985 |
| JP | 1079157/89 | 3/1989 |
| JP | 2006-508016 | 3/2006 |
| JP | 2009-520000 | 5/2009 |
| RU | 2374233 C1 | 11/2009 |
| WO | WO 02/076949 A1 | 10/2002 |
| WO | WO 03/026648 A1 | 4/2003 |
| WO | WO 2007/071662 A1 | 6/2007 |
| WO | WO 2008/034863 A2 | 3/2008 |
| WO | WO 2009/115515 A1 | 9/2009 |
| WO | WO 2010/012797 A2 | 2/2010 |

OTHER PUBLICATIONS

Otooni et al. "Efficient and simple methods . . . " Tetrhedron 54, p. 13915-13928 (1998).*
Otooni et al. "Efficient and simple methods . . . " Tetrahedron 54, p. 13915-13928 (1998).*
Handbook of green chemicals, p. 640 (2004).*
International Search Report issued Mar. 11, 2011, PCT/EP2011/051100.
Chinese Office Action dated Feb. 20, 2014 from Chinese Patent Application No. 201180007336.5.
Kost and A.N. et al., "Reaction of hydrazine derivatives, XXXVI Hydrogenation of 1-acylpyrazolines and preparation of pyrazolidines", *Zhurnal Obshchei Khimii*, vol. 33, pp. 248-252, published Dec. 1963.
Abstract of Russian Patent Publication No. RU 2374233 C1.
Abstract of Japanese Nation Phase Publication No. 2009-520000.
Abstract of Japanese Laid-Open Patent Publication No. 79157/89.
Abstract of Japanese National Phase Patent Publication No. 2006-508016.

(Continued)

*Primary Examiner* — Celia Chang
(74) *Attorney, Agent, or Firm* — Finnegan, Henderson, Farabow, Garrett & Dunner LLP

(57) ABSTRACT

This invention relates to organic chemistry, in particular to processes for the preparation of pyrazoline carboxamidine derivatives of formula (I), known as potent 5-HT6 antagonists. The invention also relates to novel intermediates of these compounds. wherein the symbols have the meanings given in the description.

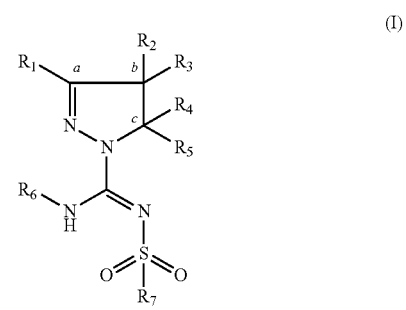

(I)

6 Claims, No Drawings

(56) References Cited

OTHER PUBLICATIONS

Database Casreact/CA/Registry (STN), AN 152:12343.
Japanese Office Action dated Nov. 6, 2014 from Japanese Patent Application No. 2012-550433.
Löränd et al., "2-Substituted indazoles. Synthesis and antimicrobial activity", Eur. J. Med. Chem., 34, pp. 1009-1018, (1999).
Japanese Office Action dated Mar. 11, 2015 from Japanese Patent Application No. 2012-550433.
File Registry on STN, RN 1192372-60-3, Entered STN: Nov. 13, 2009.
File Registry on STN, RN 1192372-61-4, Entered STN: Nov. 13, 2009.
File Registry on STN, RN 1192372-64-7, Entered STN: Nov. 13, 2009.
File Registry on STN, RN 1192372-65-8, Entered STN: Nov. 13, 2009.
File Registry on STN, RN 1185756-89-1, Entered STN: Sep. 18, 2009.
File Registry on STN, RN 1185756-90-4, Entered STN: Sep. 18, 2009.
File Registry on STN, RN 1185756-92-6, Entered STN: Sep. 18, 2009.
File Registry on STN, RN 1185756-94-8, Entered STN: Sep. 18, 2009.
File Registry on STN, RN 1107065-12-2, Entered STN: Feb. 17, 2009.
File Registry on STN, RN 119658-65-0, Entered STN: Mar. 17, 1989.
File Registry on STN, RN 220898-81-7, Entered STN: Apr. 1, 1999.
File Registry on STN, RN 220898-91-9, Entered STN: Apr. 1, 1999.
File Registry on STN, RN 186311-91-1, Entered STN: Feb. 20, 1997.
File Registry on STN, RN 96632-49-4, Entered STN: Jun. 3, 1985.
File Registry on STN, RN 96632-50-7, Entered STN: Jun. 3, 1985.
Seebacher, Werner et al., "New 1,3-Thiazoles and 1,3-Thiazines from 1-Thiocarbamoylpyrazoles." Monatshefte für Chemie, 134, p. 1623-1628 (2003).
Search Results in STN database; 4,5-dihydro-1H-pyrazole-1-carbothioamide (CAS 74982-35-7, entered in the STN database Nov. 16, 1984), 4-ethyl-4,5-dihydro-5-propyl-1H-pyrazole-1-carbothioamide (CAS 94626-82-1, entered in the STN database Feb. 3, 1985), 4,5-dihydro-3,5,5-trimethyl-1H-pyrazole-1-carbothioamide (CAS 92349-22-9, entered in the STN database Dec. 17, 1984), and 4,5-dihydro-4-(1-methylethyl)-5-(2-methylpropyl)-1H-pyrazole-1-1carbothioamide (CAS 94504-27-5, entered in the STN database Jan. 26, 1985).

\* cited by examiner

SYNTHESIS OF SUBSTITUTED PYRAZOLINE CARBOXAMIDINE DERIVATIVES

This application is a national stage filing under 35 U.S.C. §371 of International Application No. PCT/EP2011/051100, filed on Jan. 27, 2011, which claims priority of U.S. Provisional Patent Application No. 61/299,363 and European Patent Office Application No. 10152097.1, both filed on Jan. 29, 2010. The contents of these applications are each incorporated herein by reference.

This invention relates to organic chemistry, in particular to processes for the preparation of pyrazoline carboxamidine derivatives, known as potent 5-$HT_6$ antagonists. The invention also relates to novel intermediates of these compounds.

BACKGROUND

Sulfonylpyrazoline carboxamidine derivatives as potent 5-$HT_6$ antagonists were first disclosed in WO 2008/034863. Related (hetero)arylsulfonylpyrazoline carboxamidines with the same pharmacological activity were disclosed in WO 2009/115515. The synthetic routes disclosed in these applications have reasonable yields, but they are not ideally suited for synthesis on the scale required for drugs in clinical development, let alone on the scale required for marketed drugs.

The objective of the present invention was to develop a novel synthetic route to sulfonylpyrazoline carboxamidine derivatives with improved atom efficiency [Trost, B. M. *Science* 1991, 254, 1471; Sheldon, R. A. *Pure Appl. Chem.* 2000, 72, 1233] and higher yield compared to the known routes, employing readily available or accessible building blocks under mild reaction conditions, and limiting the use and release of harmful chemicals.

DISCLOSURE

It was found that a novel, more atom efficient synthetic route produced (aryl)sulfonylpyrazoline carboxamidine derivatives in substantially higher yields than the known routes under milder conditions more amenable to scale-up. The invention relates to a process for the preparation of a compound of formula (I):

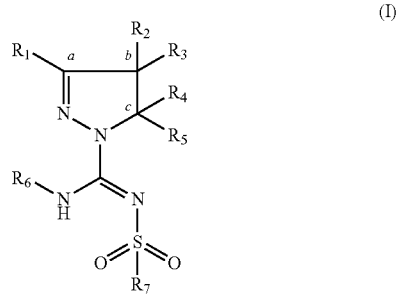

or a tautomer, stereoisomer, or a pharmacologically acceptable salt of any of the foregoing, wherein:

$R_1$ is chosen from hydrogen or an alkyl($C_{1-4}$) group, optionally substituted with one to three fluoro atoms or an hydroxy group, $R_2$ represents hydrogen or an alkyl($C_{1-4}$) group, optionally substituted with one to three fluoro atoms, an hydroxy group, a benzyloxymethyl group, an amino group, a monomethyl amino group, a dimethylamino group or a Boc-, Fmoc- or Cbz-protected amino group, which alkyl ($C_{1-4}$) group may incorporate a keto group, a sulfonyl group or an N, O or S atom, $R_3$ represents hydrogen or an alkyl($C_{1-4}$) group, optionally substituted with one to three fluoro atoms, an hydroxy group, a benzyloxymethyl group, an amino group, a monomethyl amino group, a dimethylamino group or a Boc-, Fmoc- or Cbz-protected amino group, which alkyl ($C_{1-4}$) group may incorporate a keto group, a sulfonyl group or an N, O or S atom, or $R_1$ and $R_2$, together with the carbon atoms marked 'a' and 'b' form a $C_{5-8}$-cycloalkyl ring, optionally substituted with one to three fluoro atoms, an hydroxy group or an alkyl($C_{1-4}$) group, or, $R_2$ and $R_3$, together with the carbon atom marked 'b' form a $C_{3-8}$-cycloalkyl ring, optionally substituted with one to four fluoro atoms, one or two methyl groups or an hydroxy group, or $R_2$ and $R_3$, together with the carbon atom marked 'b' form a $C_{5-8}$-heterocycloalkyl ring optionally substituted with one to four fluoro atoms, one or two methyl groups, a benzyl group or an hydroxy group, $R_4$ represents hydrogen or an alkyl($C_{1-4}$) group, optionally substituted with one to three fluoro atoms or an hydroxy group, or $R_4$ represents a monocyclic aryl or heteroaryl group optionally substituted with one to five substituents Q which can be the same or different, chosen from halogen, trifluoromethyl, trifluoromethoxy, cyano, $C_{1-3}$-alkyl, $C_{1-3}$-alkoxy, hydroxy, amino, acetyl, acetamido, trifluoroacetamido, —$CONH_2$, —$SO_2NH_2$ or —$CO_2H$, or $R_3$ and $R_4$, together with the carbon atoms marked 'b' and 'c' form a $C_{5-8}$-cycloalkyl ring, optionally substituted with one to four fluoro atoms, one or two methyl groups or an hydroxy group, or $R_3$ and $R_4$, together with the carbon atoms marked 'b' and 'c' form a $C_{5-8}$-heterocycloalkyl ring optionally substituted with one to four fluoro atoms, one or two methyl groups, a benzyl group or an hydroxy group, $R_5$ represents hydrogen or methyl, $R_6$ is chosen from hydrogen atom, or an alkyl($C_{1-4}$) group, optionally substituted with one to three fluoro atoms or an hydroxy group, $R_7$ represents a monocyclic, or a fused-bicyclic aromatic or hetero-aromatic group, which groups are unsubstituted or substituted with one to five substituents Q, as defined above, or $R_7$ represents a 2-aryl-ethenyl group or a 2-aryl-ethynyl group, or $R_7$ represents a piperidinyl group unsubstituted or substituted with one to four fluoro atoms or a $CF_3$ group, or $R_7$ represents a 2,3-dihydroindolyl group or a benzimidazol-2-one group comprising the steps of:

(i) reacting a substituted 4,5-dihydro-(1H)-pyrazole of formula (II$^a$) or the isomeric substituted 4,5-dihydro-3H-pyrazole of formula (II$^b$):

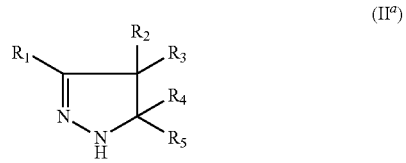

-continued

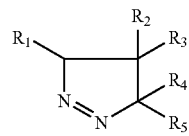
(II$^b$)

wherein R$_1$, R$_2$, R$_3$, R$_4$ and R$_5$ have the meanings as given above, with an isothiocyanate of formula R$_6$—N=C=S, wherein R$_6$ has the meaning as given above, to give a substituted 4,5-dihydro-(1H)pyrazole-1-carbothioic acid amide of formula (III$^a$) or the tautomeric substituted 4,5-dihydro-(1H)pyrazole-1-carboximidothioic acid of formula (III$^b$):

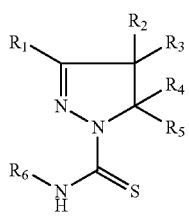
(III$^a$)

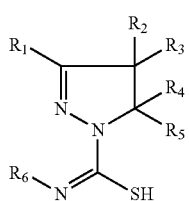
(III$^b$)

(ii) reacting the obtained compound of formula (III$^a$) or (III$^b$), with an alkylating reagent of general formula R$^x$-L, wherein R$^x$ represents a linear (C$_{1-8}$)-alkyl group and L represents a leaving group, preferably chosen from Br, Cl or I, to give a compound of formula (IV):

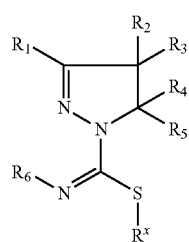
(IV)

(iii) reacting the obtained compound of formula (IV) with a sulfonamide derivative of formula R$_7$SO$_2$NH$_2$, wherein R$_7$ has the meaning given above, to give a compound of formula (I):

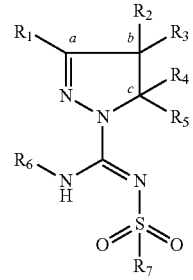
(I)

In step (i) the reactants, as free bases or salts thereof, are dissolved in a suitable solvent, preferably a polar solvent, most preferably a (C$_{1-8}$)-alcohol, or a mixture thereof, optionally containing water. The reaction is preferably carried out at an elevated temperature, most preferably at reflux, for about 1-16 hours, preferably about 2.5 to about 5 hours.

Also in step (ii) the reactants, as free bases or salts thereof, are dissolved in a suitable solvent, preferably a polar solvent, such as acetonitrile, methyl ethyl ketone, a (C$_{1-8}$)-alcohol, or a mixture of polar solvents, most preferably methanol or acetonitrile. The reaction is preferably carried out at an elevated temperature, but can be carried out at room temperature. A temperature between approximately 40° C. and approximately 50° C. is preferred. Most preferred is a reaction temperature of 50° C. Reaction time is between about 1 and about 5 hours. Preferred alkylating reagents of general formula R$^x$-L, wherein R$^x$ represents a linear (C$_{1-8}$)-alkyl group and L represents a 'leaving group', preferably chosen from Br, Cl or I, are methyl halogenides. Most preferred is methyl iodide.

In step (iii) the reactants, as free bases or salts thereof, are dissolved in a suitable solvent, preferably a polar solvent, most preferably acetonitrile. The reaction is preferably carried out at an elevated temperature, preferably at reflux, for about 16-72 hours, preferably for about 10 to about 16 hours.

The invention relates to racemates, mixtures of diastereomers as well as the individual stereoisomers of the compounds having formula (I). The invention also relates to the E isomer, Z isomer and E/Z mixtures of compounds having formula (I) and their salts. The invention also relates to racemates, mixtures of diastereomers as well as the individual stereoisomers of the compounds having formula (III$^a$), (III$^b$) and (IV) and salt forms of compounds having formula (III$^a$), (III$^b$) and (IV).

The invention also relates to a process for the preparation of a compound of formula (I) wherein R$_1$ is chosen from hydrogen or an alkyl(C$_{1-2}$) group, R$_2$ represents hydrogen or an alkyl(C$_{1-3}$) group, optionally substituted with one to three fluoro atoms or an hydroxy group, R$_3$ represents hydrogen or an alkyl(C$_{1-3}$) group, optionally substituted with one to three fluoro atoms or an hydroxy group, or R$_1$ and R$_2$, together with the carbon atoms marked 'a' and 'b' form a C$_{5-8}$-cycloalkyl ring, or, R$_2$ and R$_3$, together with the carbon atom marked 'b' form a C$_{3-8}$-cycloalkyl ring, optionally substituted with one to four fluoro atoms or an hydroxy group, or R$_2$ and R$_3$, together with the carbon atom marked 'b' form a C$_{5-8}$-heterocycloalkyl ring optionally substituted with a methyl or a benzyl group or an hydroxy group, R$_4$ represents hydrogen or an alkyl(C$_{1-2}$) group, or R$_4$ represents a monocyclic aryl or heteroaryl group optionally substituted with one to three substituents Q as defined above, or R$_3$ and R$_4$, together with the carbon atoms marked 'b' and 'c' form a C$_{5-8}$-cycloalkyl ring, or R$_3$ and R$_4$, together with the carbon atoms marked 'b' and 'c' form a C$_{5-8}$-heterocycloalkyl ring optionally substituted with a methyl or a benzyl group, R$_5$ represents hydrogen, R$_6$ is chosen from hydrogen or an alkyl(C$_{1-3}$) group optionally substituted with one to three fluoro atoms, R$_7$ represents a monocyclic, or a fused-bicyclic aromatic or hetero-aromatic group, which groups are unsubstituted or substituted with one to five substituents Q, as defined above or R$_7$ represents a 2-aryl-ethenyl group or a 2-aryl-ethynyl group, or R$_7$ represents a piperidinyl group, or R$_7$ represents a 2,3-dihydroindolyl group or a benzimidazol-2-one group Another embodiment relates to a process for the preparation of a compound of formula (I) wherein the moiety:

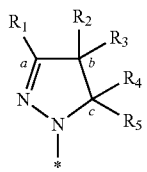

is chosen from:

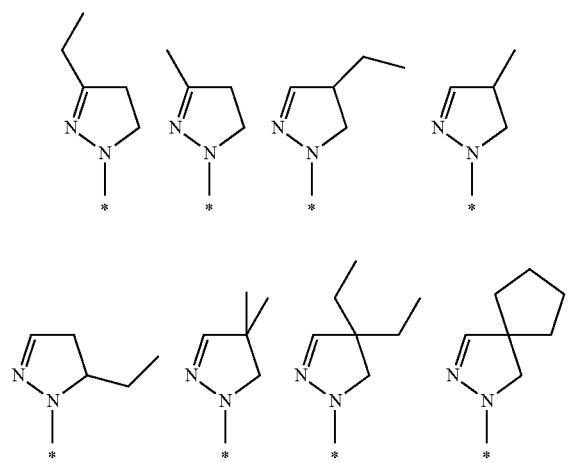

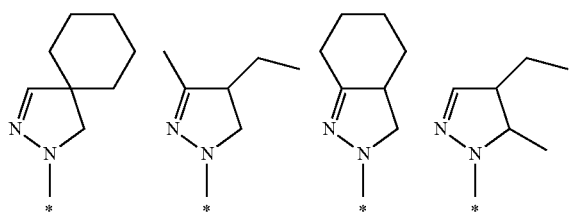

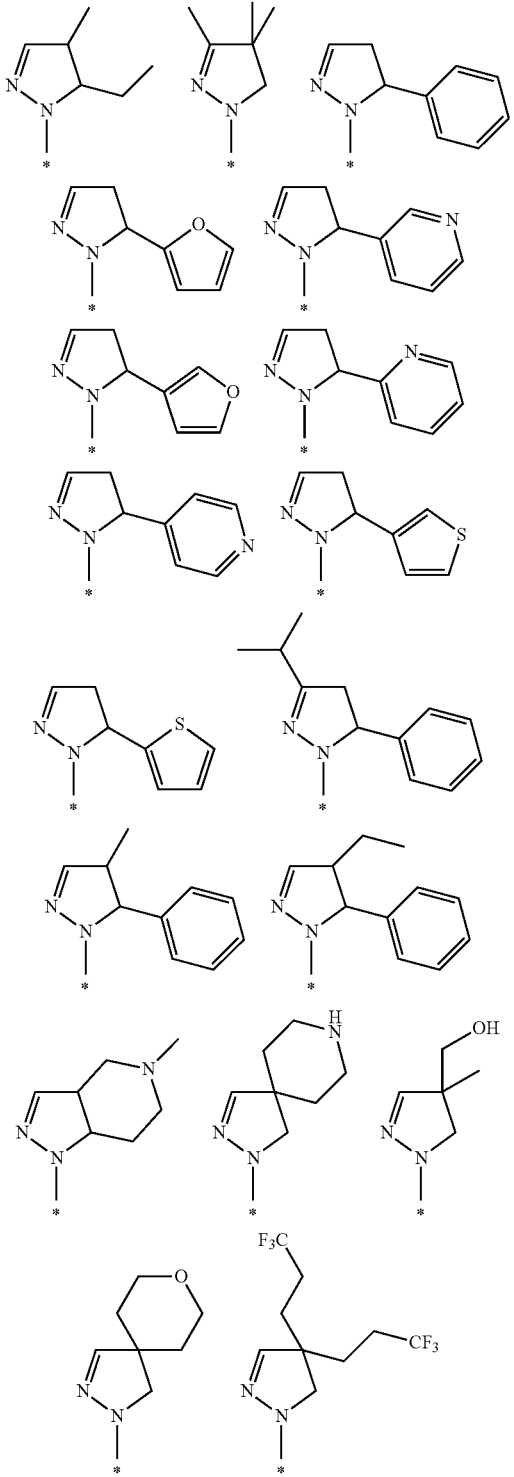

R$_6$ is chosen from hydrogen or an alkyl(C$_{1-3}$) group optionally substituted with one to three fluoro atoms, R$_7$ represents a monocyclic, or a fused-bicyclic aromatic or hetero-aromatic group, which groups are unsubstituted or substituted with one to five substituents Q, as defined above, or R$_7$ represents a 2-aryl-ethenyl group or a 2-aryl-ethynyl group, or R$_7$ represents a piperidinyl group, or R$_7$ represents a 2,3-dihydroindolyl group or a benzimidazol-2-one group Another embodiment relates to a process for the preparation of a compound of formula (I) wherein the moiety:

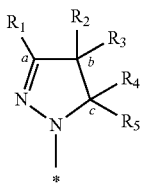

is chosen from:

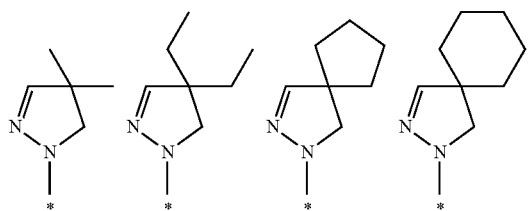

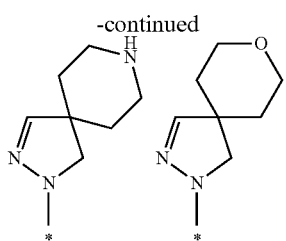

$R_6$ is chosen from hydrogen or an alkyl($C_{1-2}$) group optionally substituted with three fluoro atoms, $R_7$ represents a monocyclic, or a fused-bicyclic aromatic or hetero-aromatic group, which groups are unsubstituted or substituted with one or two substituents chosen from methyl, methoxy, fluoro, chloro, bromo, cyano, acetamido, trifluoroacetamido, trifluoromethyl, amino or hydroxy A specific embodiment relates to a process for the preparation of a compound having formula:

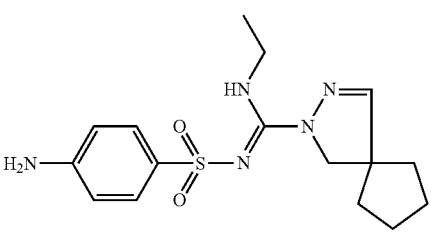 [SMILES: CCN/C(=N\S(=O)(=O)c1ccc(N)cc1)N1CC2(C=N1)CCCC2]

and tautomers and salt forms thereof, comprising the steps of:

(i) reacting 2,3-diaza-spiro[4.4]non-2-ene or 2,3-diaza-spiro[4.4]non-1-ene, or salts thereof, synthesized as disclosed in WO 2008/034863, with ethyl isothiocyanate, to yield 2,3-diazaspiro[4.4]non-3-ene-2-carbothioic acid ethylamide or its tautomer (ii) reacting it with iodomethane or methyl p-toluenesulfonate yielding N-ethyl-2,3-diaza-spiro[4.4]non-3-ene-2-carboximido-thioic acid methyl ester,

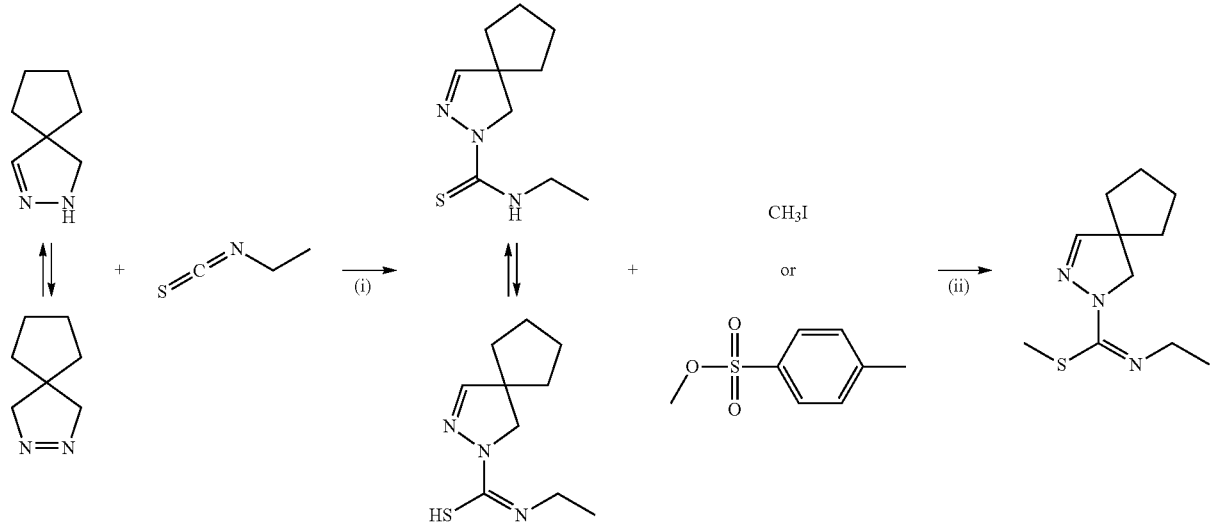

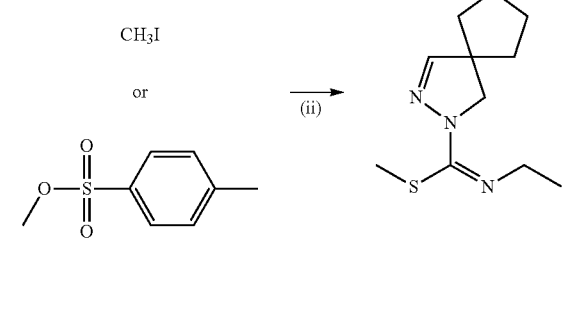

(iii) reacting the latter, as free base or salt thereof, with 4-acetamidobenzenesulfonamide (CAS 121-61-9, commercially available) yielding N-(4-{[(2,3-diaza-spiro[4.4]non-3-en-2-yl)-ethylamino-methylene]sulfamoyl}-phenyl)-acetamide (iv) deprotecting the latter under acidic conditions, yielding 4-amino-N-[(2,3-diaza-spiro[4.4]non-3-en-2-yl)-ethylamino-methylene]-benzenesulfonamide

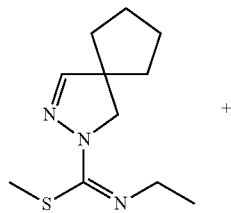

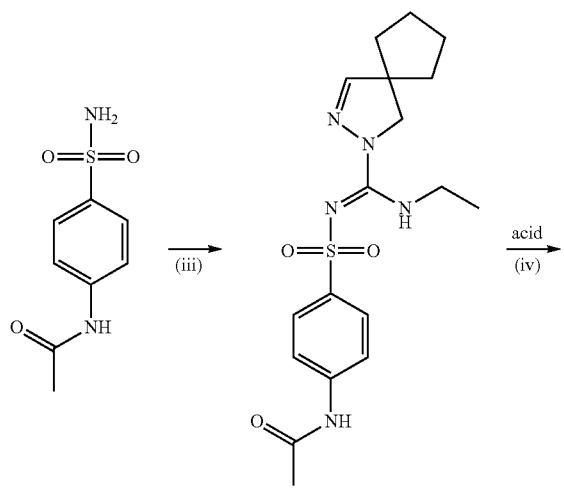

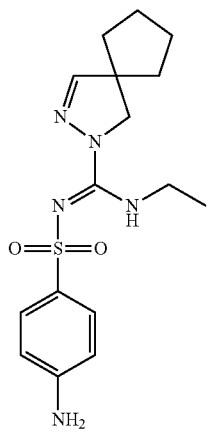

Another embodiment relates to compounds of formulae (III$^a$), (III$^b$) or (IV):

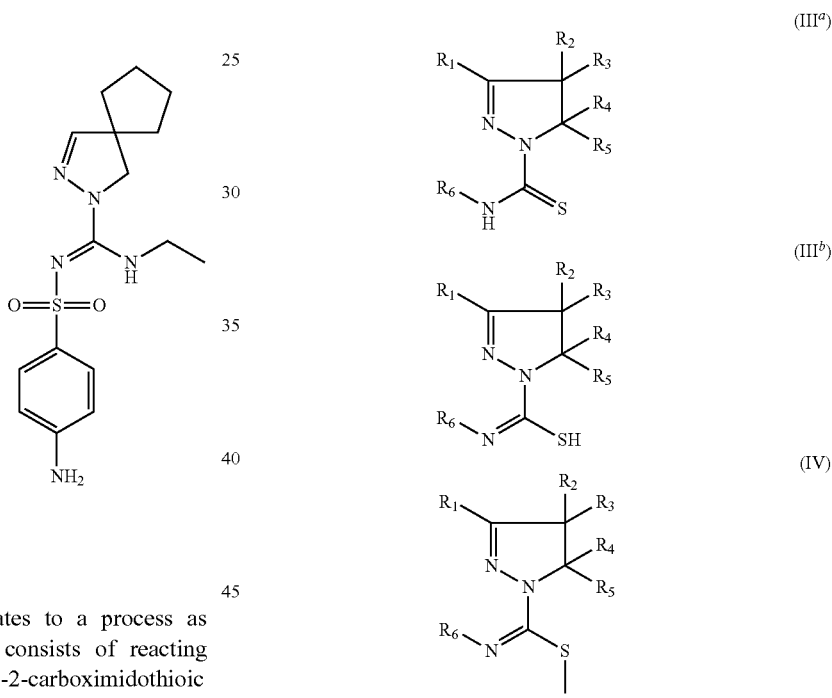

Another specific embodiment relates to a process as described above wherein step (iii) consists of reacting N-ethyl-2,3-diaza-spiro[4.4]non-3-ene-2-carboximidothioic acid methyl ester with sulfanilamide (CAS 129-56-6, commercially available), yielding 4-amino-N-[(2,3-diaza-spiro[4.4]non-3-en-2-yl)-ethylamino-methylene]benzene-sulfonamide:

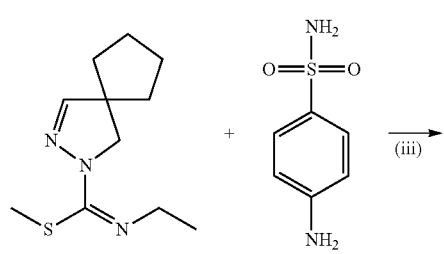

wherein $R_1$, $R_2$, $R_3$, $R_4$, $R_5$ and $R_6$ have the meanings as given above, as well as tautomers, stereoisomers, and salts of any of the foregoing, such compounds being useful in the synthesis of compounds of formula (I).

The compounds and intermediates described herein can, if desired, be isolated and purified by any suitable separation or purification procedure such as, filtration, extraction, crystallization, column chromatography, thin-layer chromatography, thick-layer chromatography, preparative low or high-pressure liquid chromatography, or a combination of these procedures. The preparations and examples illustrate how to separate and isolate the compounds, but other equivalent procedures could be used, too.

The compounds of the invention may contain one or more asymmetric centers and can thus occur as racemates and racemic mixtures, single enantiomers, diastereomeric mixtures and individual diastereomers.

Depending on the nature of the various substituents, the molecule can have additional asymmetric centers. Each such asymmetric center will independently produce two optical isomers. All of the possible optical isomers, enantiomers and diastereomers, in mixtures and as pure or partially purified compounds, belong to this invention. The present invention comprehends all such isomeric forms of these compounds. Formula (I) shows the structure of the class of compounds without preferred stereochemistry. The independent syntheses of these optical isomers, or their chromatographic separations, may be achieved by known methods, appropriately modifying the methodology disclosed therein. Their absolute stereochemistry may be determined by the X-ray crystallography of crystalline products or crystalline intermediates, derivatized if necessary, with a reagent containing an asymmetric center of known absolute configuration. Racemic mixtures of the compounds can be separated into the individual enantiomers by well-known methods, such as the coupling of a racemic mixture of compounds to an enantiomerically pure compound to form a diastereomeric mixture, followed by separation of the individual diastereomers by standard methods, such as fractional crystallization or chromatography. The coupling often consists of the formation of salts using an enantiomerically pure acid or base, for example (−)-di-p-toluoyl-D-tartaric acid or (+)-di-p-toluoyl-L-tartaric acid. The diasteromeric derivatives may then be converted to the pure enantiomers by cleavage of the added chiral residue. The racemic mixture of the compounds can also be separated directly by well-known chromatographic methods utilizing chiral stationary phases. Alternatively, any enantiomer of a compound may be obtained by stereoselective synthesis using optically pure starting materials or reagents of known configuration by methods well-known in the art.

Cis and trans isomers of the compound of formula (I), or a pharmaceutically acceptable salt thereof, also belong to the invention, and this also applies to tautomers of the compounds of formula (I).

The synthetic strategy in this novel route is essentially different from the known routes, introducing the $R_6$ and $R_7$ substituents in different stages of the synthesis and/or through a different class of building blocks. Starting from an intermediate of tautomeric formula (IIa) or (IIb), which is a common building block in both this novel route and the previously disclosed routes, the $R_6$ substituent is introduced from an isothiocyanate instead of from an amine (routes 1 and 3 disclosed in WO 2009/115515) or a thiourea (route 2 disclosed in WO 2009/115515) building block. As such, novel intermediates of tautomeric formula (IIIa) or (IIIb) are formed with maximum atom efficiency (100%) under neutral conditions, amenable to scale-up. The novel intermediates of formula (IV), in which an easily substituted S-alkyl leaving group is generated, are readily obtained from (IIIa)/(IIIb) under mild alkylation conditions. In contrast, route 3 disclosed in WO 2009/115515 requires significantly harsher conditions to generate, in situ, the halogen leaving group to be substituted with the $R_6$ amine building block in the final stage. The final step of the novel route is substitution of the S-alkyl leaving group from intermediate (IV), but unlike route 1 disclosed in WO 2009/115515 in which an $R_6$ amine building block displaces the S-alkyl moiety, this novel route finishes with introduction of the $R_7$ sulfonamide building block, noteworthily under neutral conditions and mild heating. Routes 1 and 3 disclosed in WO 2009/115515 take along the $R_7$ sulfonyl substituent under more harsh conditions from an earlier stage in the route, whereas in contrast route 2 disclosed in WO 2009/115515 does also introduce the $R_7$ sulfonyl substituent in the final stage but with a more reactive $R_7$ sulfonyl chloride building block under basic conditions (thereby limiting the use of unprotected nucleophilic moieties in the $R_7$ residue). As such, the novel route comprises an improvement with respect to functional group tolerance in the $R_7$ substituent—illustrated here in several examples such as the synthesis of compound 4 where $R_7$ substituents containing aminoaryl functionalities have been introduced chemoselectively without the need for protection.

Apart from an obvious difference in synthetic strategy and the associated mildness of the reaction conditions under which the steps can generally be carried out, this novel route clearly profits from several other aspects that become of particular relevance during scale-up. Route 3 disclosed in WO 2009/115515 employs corrosive halogenating agents and as such carries its limitations. Route 1 disclosed in WO 2009/115515 uses toxic $CS_2$ under strongly basic conditions and as well has the disadvantage that two molar equivalents of alkylating agent are incorporated and two steps are involved each in which one molar equivalent of alkanethiol is released. The novel route, avoiding strongly basic or acidic conditions, does not employ $CS_2$, incorporates only one equivalent of alkylating agent and contains only one step in which a molar equivalent of alkanethiol is released. Although the latter arguments also hold for route 2 disclosed in WO 2009/115515, the requirement to use reactive sulfonyl chloride building blocks in this route may be a limiting factor—not only in handling but in particular cases also in functional group tolerability. As illustrated for the synthesis of compound 4, incorporation of the 4-aminophenylsulfonyl moiety via route 2 in WO 2009/115515, requires protection of the amino group. Removal of the N-acetyl protective group (coming from N-acetylsulfanilyl chloride, CAS 121-60-8, commercially available) implicates an additional step to be carried out, under strongly acidic (corrosive) conditions carrying a risk for concomitant sulfonamide hydrolysis, thereby resulting in only moderate yields as illustrated.

In an era during which availability of raw materials and environmental concerns become increasingly important, particularly for processes carried out on large scale, atom efficiency is a recognized parameter to evaluate synthetic routes. The atom efficiency [Sheldon, R. A. *Pure Appl. Chem.* 2000, 72, 1233] (expressed as percentage) can be calculated by taking the ratio of the molecular weight of the final product over the added molecular weights of all used building blocks that transfer the atoms of which the product is constituted. As compared for compound 4 of the current invention, based on the required steps to come to the final product excluding the synthesis of the intermediate of formula (IIa)/(IIb) common in all routes, it is illustrated that the novel route from the current invention outperforms the routes disclosed in the prior art in terms of both atom efficiency and overall yield:

Route 1 disclosed in WO 2009/115515:

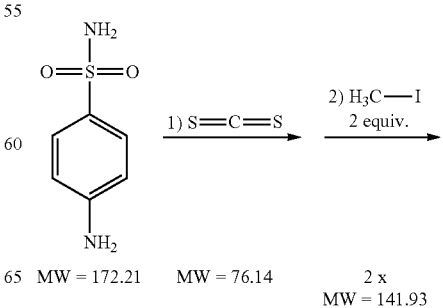

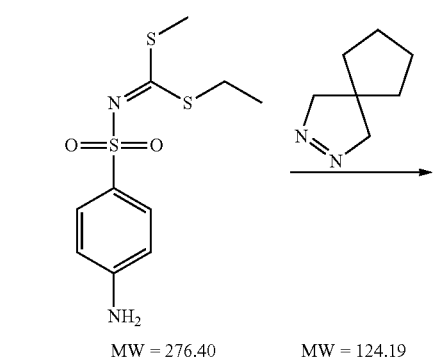
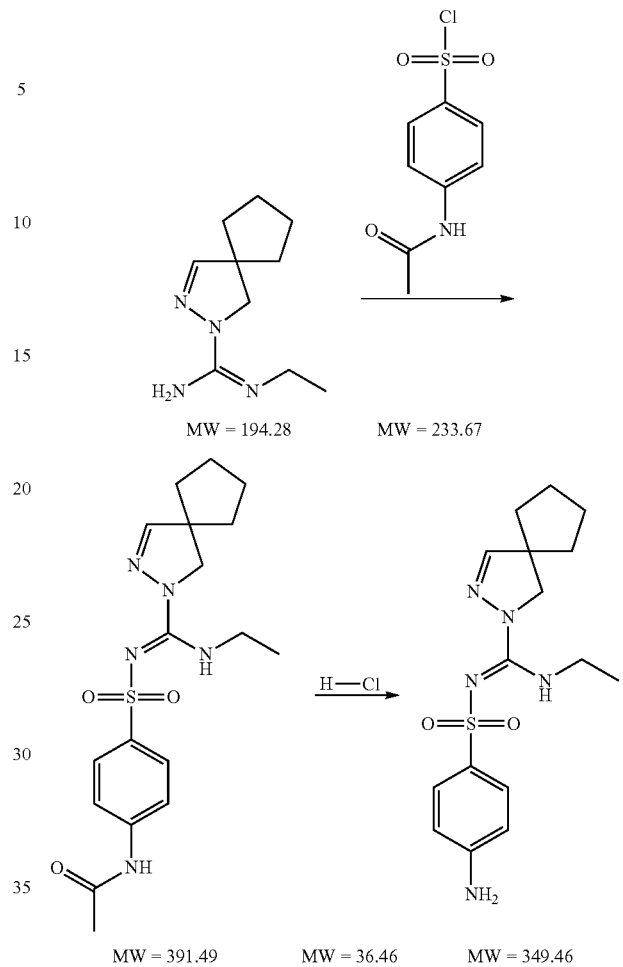
Atom efficiency: [349.46/(172.21+76.14+(2×141.93)+124.19+45.08)]×100%=50%
Yield: 40%×25%×67%=7%
Route 2 disclosed in WO 2009/115515:
Atom efficiency: [349.46/(104.18+141.93+124.19+233.67+36.46)]×100%=55%
Yield: 100%×78%×77%×55%=33% (Yields of the final 2 steps for this particular example not illustrated in WO 2009/115515 but specified in this disclosure)
Novel Route:
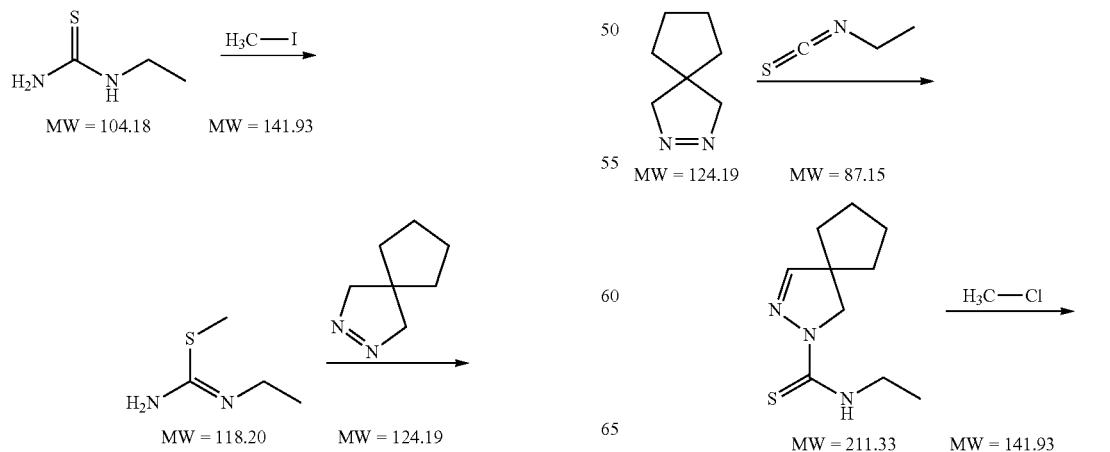

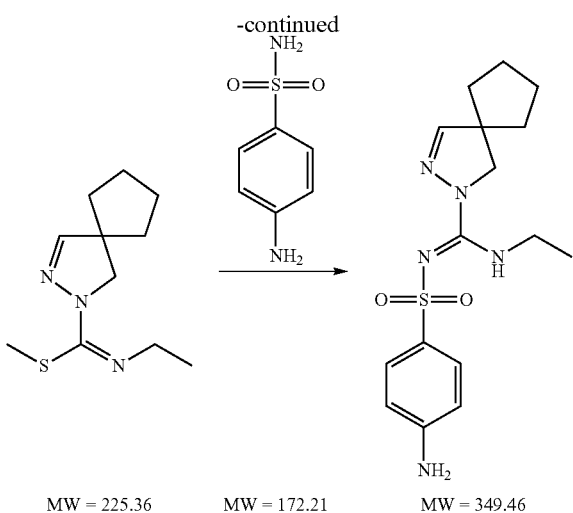

MW = 225.36   MW = 172.21   MW = 349.46

Atom efficiency: [349.46/(124.19+87.15+141.93+172.21)]×100%=67%

Yield: 83%×97%×67%=54% (first step: scale-up from pyrazoline HCl salt)

DEFINITIONS

General terms used in the description of compounds herein disclosed bear their usual meanings. The term alkyl denotes a univalent saturated, branched or straight, hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, hexyl, isohexyl, heptyl, octyl, nonyl, decyl, undecyl, dodecyl, tridecyl, tetradecyl, pentadecyl, hexadecyl, heptadecyl, octadecyl, etc. When qualified as 'lower', the alkyl group will contain from 1 to 6 carbon atoms. The same carbon content applies to the parent term 'alkane', and to derivative terms such as 'alkoxy'. The carbon content of various hydrocarbon containing moieties is indicated by a prefix designating the minimum and maximum number of carbon atoms present in the moiety, i.e., the prefix $C_{x-y}$ defines the number of carbon atoms present from the integer "x" to the integer "y" inclusive. 'Alkyl($C_{1-3}$)' for example, includes methyl, ethyl, n-propyl or isopropyl, and 'alkyl($C_{1-4}$)' includes 'methyl, ethyl, n-propyl, isopropyl, n-butyl, 2-butyl, isobutyl or tert-butyl'.

The term 'Aryl' embraces mono- or polycyclic aromatic groups, including phenyl, naphthyl, 1,2,3,4-tetrahydro-naphtyl, indenyl, fluorenyl, anthracenyl, phenanthrenyl, naphthacenyl and azulenyl. 'Heteroaryl' embraces mono- or polycyclic hetero-aromatic, including furyl, thienyl, pyrrolyl, oxazolyl, thiazolyl, imidazolyl, imidazo[2,1-b][1,3]thiazolyl, pyrazolyl, isoxazolyl, isothiazolyl, pyridyl, pyridazinyl, pyrimidinyl, pyrazinyl, 1,3,5-triazinyl, indazolyl, indolyl, indolizinyl, isoindolyl, benzo[b]furanyl, 1,2,3,4-tetrahydroiso-quinolinyl, indanyl, indenyl, benzo[b]thienyl, 2,3-dihydro-1,4-benzodioxin-5-yl, benzimidazolyl, cinnolinyl, carbazolyl, acridinyl, phenazinyl, phenothiazinyl, phenoxazinyl, benzothiazolyl, benzo[1,2,5]thia-diazolyl, purinyl, quinolinyl, isoquinolinyl, quinolizinyl, phtalazinyl, quinazolinyl, quinoxalinyl, 1,8-naphthyridinyl and pteridinyl.

'Halo' or 'Halogen' refers to chloro, fluoro, bromo or iodo; 'hetero' as in 'heteroalkyl, heteroaromatic', etc. includes containing one or more N, O or S atoms. 'heteroalkyl' includes alkyl groups with heteroatoms in any position, thus including N-bound O-bound or S-bound alkyl groups.

The term "substituted" means that the specified group or moiety bears one or more substituents. Where any group may carry multiple substituents, and a variety of possible substituents can be provided, the substituents are independently selected, and need not to be the same. The term "unsubstituted" means that the specified group bears no substituents. With reference to substituents, the term "independently" means that when more than one of such substituents are possible, they may be the same or different from each other.

'$C_{3-8}$-cycloalkyl' includes cyclopropyl, cyclobutyl, cyclopentyl, cyclohexyl, cycloheptyl or cyclooctyl; '$C_{5-8}$ heterocycloalkyl' refers to heteroatom containing rings including piperidinyl, morpholinyl, azepanyl, pyrrolidinyl, thiomorpholinyl, piperazinyl, tetrahydrofuryl, tetrahydro-pyranyl;

The terms "oxy", "thio" and "carbo" as used as part of another group respectively refer to an oxygen atom, a sulphur atom and a carbonyl (C=O) group, serving as linker between two groups, for instance hydroxyl, oxyalkyl, thioalkyl, carboxyalkyl, etc. The term "amino" as used alone, or as part of another group, refers to a nitrogen atom that may be either terminal, or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine. The terms "sulfinyl" and "sulfonyl" as used as part of another group respectively refer to an —SO— or an —$SO_2$— group.

To provide a more concise description, the terms 'compound' or 'compounds' include tautomers, stereoisomers, N-oxides, isotopically-labelled analogues, or pharmacologically acceptable salts, also when not explicitly mentioned.

The term "leaving group" (L) comprises a charged or uncharged atom or group departing during a substitution or displacement reaction. The term refers to groups readily displaceable by a nucleophile, such as an amine, a thiol or an alcohol nucleophile. Such leaving groups are well known. Examples include N-hydroxysuccinimide, N-hydroxybenzotriazole, halides (Br, Cl, I), triflates, mesylates, tosylates, etc.

To give a more concise description, some of the quantitative expressions given herein are not qualified with either "about" or "approximately". It is understood that whether either of these terms is used explicitly or not, every quantity given is meant to refer to the actual value, and also to the approximation to such given value that would reasonably be inferred based on ordinary skill, including approximations due to experimental or measurement conditions for such given value. Throughout the description and the claims of this specification, the word "comprise" and variations of the word, such as "comprising" and "comprises", is not intended to exclude other additives, components, integers or steps.

ABBREVIATIONS

ACN acetonitrile
API atmospheric pressure ionisation
Boc tert-butoxycarbonyl
Cbz benzyloxycarbonyl
CUR curtain gas
DCM dichloromethane
DiPEA N,N-diisopropylethylamine
DMSO dimethylsulfoxide
EA ethylacetate
ESI Electron Spray Ionization
Fmoc 9-fluorenylmethoxycarbonyl
FP focusing potential MeOH methanol
m.p. melting point c.q. melting range
MS Mass Spectrometry
PA petroleum aether (40-60)
$R_f$ retention factor (thin layer chromatography)
$R_t$ retention time (LC/MS)
RT room temperature
THF tetrahydrofuran

EXAMPLE 1

Analytical Methods $^1$H NMR spectra were recorded on a Varian UN400 instrument (400 MHz) or a Bruker Avance DRX600 instrument (600 MHz) using DMSO-$d_6$, $CD_3CN$ or $CDCl_3$ as solvents with tetramethylsilane as an internal standard. Chemical shifts are given in ppm (δ scale) downfield from tetramethylsilane. Coupling constants (J) are expressed in Hz. Flash chromatography was performed using silica gel 60 (0.040-0.063 mm, Merck). Column chromatography was performed using silica gel 60 (0.063-0.200 mm, Merck) or alumina (act III). Sepacore chromatographic separations were carried out using Supelco equipment, VersaFLASH™ columns, VersaPak™ silica cartridges, Büchi UV monitor C-630, Büchi Pump module C-605, Büchi fraction collector C-660 and Büchi pump manager C-615. Melting points were recorded on a Büchi B-545 melting point apparatus or determined by DSC (differential scanning calorimetry) methods.

Liquid Chromatography-Mass Spectrometry (LC-MS): The LC-MS system consisted of 2 Perkin Elmer series 200 micro pumps. The pumps were connected to each other by a 50 μl tee mixer, connected to a Gilson 215 auto sampler. The method was as follows:

| step | total time | flow (μl/min) | A (%) | B (%) |
|---|---|---|---|---|
| 0 | 0 | 2000 | 95 | 5 |
| 1 | 1.8 | 2000 | 0 | 100 |
| 2 | 2.5 | 2000 | 0 | 100 |
| 3 | 2.7 | 2000 | 95 | 5 |
| 4 | 3.0 | 2000 | 95 | 5 |

A = 100% Water with 0.025% HCOOH and 10 mmol $NH_4HCOO$ pH = ±3
B = 100% ACN with 0.025% HCOOH The auto sampler had a 2 μl injection loop, and was connected to a Waters Atlantis C18 30*4.6 mm column with 3 μm particles. The column was thermostated in a Perkin Elmer series 200 column oven at 40° C. The column was connected to a Perkin Elmer series 200 UV meter with a 2.7 μl flowcel. The wavelength was set to 254 nm. The UV meter was connected to a Sciex API 150EX mass spectrometer. The mass spectrometer had the following parameters: Scan range:150-900 a.m.u.; polarity: positive; scan mode: profile; resolution Q1: UNIT; step size: 0.10 a.m.u.; time per scan: 0.500 sec; NEB: 10; CUR: 10 IS: 5200; TEM: 325; DF: 30; FP: 225 and EP: 10. The light scattering detector was connected to the Sciex API 150. The light scattering detector was a Sedere Sedex 55 operating at 50° C. and 3 bar $N_2$. The complete system was controlled by a G3 powermac.

EXAMPLE 2

General Aspects of Syntheses

Substituted 4,5-dihydro-(1H)-pyrazoles of formula (II$^a$) or substituted 4,5-dihydro-3H-pyrazoles of formula (II$^b$) can be prepared as disclosed in WO 2008/034863, and can be reacted with isothiocyanates of formula $R_6$—N=C=S, wherein $R_6$ has the meaning as given above, to give substituted 4,5-dihydro-(1H)-pyrazole-1-carbothioic acid amides of formula (IIIa) or substituted 4,5-dihydro-(1H)-pyrazole-1-carboximidothioic acids of formula (IIIb). Compounds of formula (III$^a$) or (III$^b$) can be S-alkylated, for instance with an alkyl halide such as methyl iodide, to give compounds of formula (IV). The latter can be reacted with a sulfonamide derivative of formula $R_7SO_2NH_2$, wherein $R_7$ has the meaning as given above, resulting in compounds of formula (I). A skilled person will notice that the S-alkyl group acts as a leaving group in this particular reaction. In the scheme above, $R_1$-$R_7$ have the meanings as given above. Compounds (II$^a$) and (II$^b$) are tautomers, as are compounds (III$^a$) and (III$^b$), and as such part of the invention. Compounds of formulae (III$^a$), (III$^b$) and (IV) are new.

Scheme 1 outlines the synthesis of compounds of formula (I):

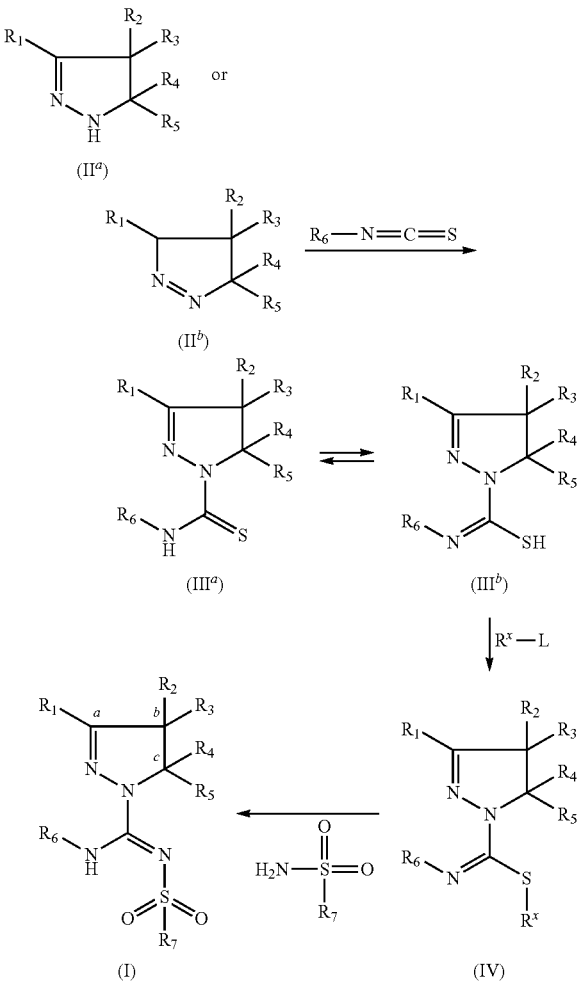

Pharmaceutically acceptable salts may be obtained using well known standard procedures, for example by mixing a compound of the present invention with a suitable acid, for instance an inorganic acid such as hydrochloric acid, or with an organic acid like fumaric acid.

The selection of particular synthetic procedures depends on factors known to skilled persons. For instance compatibility of functional groups with reagents used, the possibility to use protective groups, catalysts, activating and coupling reagents, and the ultimate structural features present in the final compound being prepared. For example, amino groups in $R_2$, $R_3$ or $R_4$ can be protected prior to reaction with $R_6$-NCS.

EXAMPLE 3

Synthesis of Compounds of the Invention 2,3-Diazaspiro[4.4]non-3-ene-2-carbothioic acid ethylamide (compound 1, small scale)

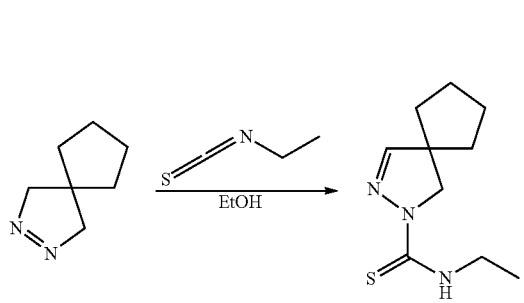

1.05 g (1 mol equiv.) 2,3-diaza-spiro[4.4]non-2-ene (synthesized as described in WO 2008/034863) and 0.95 mL (1.3 mol equiv.) ethyl isothiocyanate were added to 10 mL ethanol. The reaction mixture was refluxed for 2.5 hours under magnetic stirring. Silica gel was added and volatiles were removed in vacuo. The product was purified by flash chromatography on silica gel ($Et_2O:PA=1:2$) and, after evaporation of the volatiles, stirred with diisopropylether and collected by filtration to yield 0.57 g (32%) of 2,3-diazaspiro[4.4]non-3-ene-2-carbothioic acid ethylamide. $^1$H NMR (400 MHz, CDCl$_3$) δ 1.24 (t, J=7.2 Hz, 3H), 1.64-1.86 (m, 8H), 3.68 (dq, J=7.2, 5.5 Hz, 2H), 4.00 (s, 2H), 6.80 (s, 1H), 7.08-7.18 (br.s., 1H).

2,3-Diazaspiro[4.4]non-3-ene-2-carbothioic acid ethylamide (compound 1, larger scale)

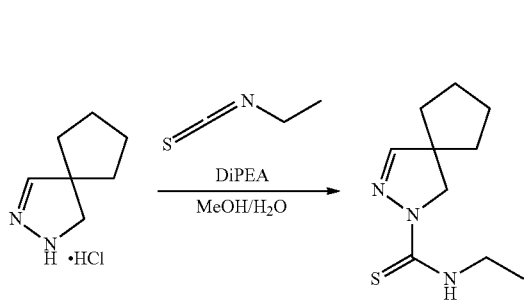

2,3-Diaza-spiro[4.4]non-1-ene hydrochloride (15.4 g, 95.9 mmol; isolated from reaction of 2,3-diaza-spiro[4.4]non-2-ene, synthesized as described in WO 2008/034863, with HCl in isopropanol/toluene) was taken up in a mixture of 70 mL methanol and 30 mL water. Ethyl isothiocyanate (10.09 g, 115.1 mmol) was added using an addition funnel, and the funnel was rinsed with 40 mL methanol. At 30° C., diisopropylethylamine (14.8 g, 114.5 mmol) was added dropwise over a period of 10 minutes, and the addition funnel was rinsed with 7 mL water. After stirring the reaction mixture for 1 hour at 30° C., the mixture was cooled to 10° C. over a period of 1 hour and subsequently stirred at this temperature for another 2 hours. The precipitate was isolated by filtration, washed twice with 20 mL of a cold 3:1 mixture of methanol and water and dried at 50° C. under reduced pressure to give 16.8 g (83%) of 2,3-diaza-spiro[4.4]non-3-ene-2-carbothioic acid ethylamide as a white to off-white solid. $^1$H NMR identical to spectrum obtained from material prepared on small scale (vide supra).

N-ethyl-2,3-diaza-spiro[4.4]non-3-ene-2-carboximidothioic acid methyl ester (compound 2)

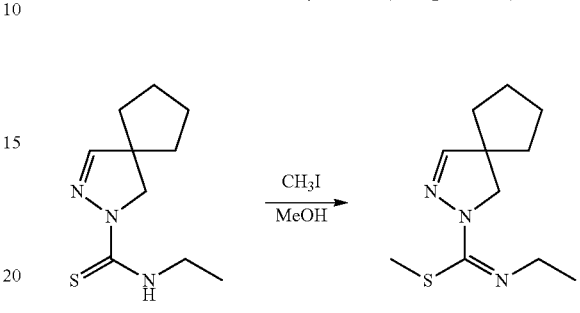

0.55 g (1 mol equiv.) 2,3-Diazaspiro[4.4]non-3-ene-2-carbothioic acid ethylamide was dissolved in 15 mL MeOH, 3.4 mL (21 mol equiv.) iodomethane was added and the magnetically stirred reaction mixture was heated at 45° C. for 2 hours. Volatiles were removed in vacuo. The residue was taken up in dichloromethane (DCM) and extracted with 5% aqueous NaHCO$_3$. The organic layer was washed twice with water, dried over Na$_2$SO$_4$, filtered and evaporated to dryness to give 0.57 g (97%) N-ethyl-2,3-diaza-spiro[4.4]non-3-ene-2-carboximidothioic acid methyl ester. $^1$H NMR (400 MHz, CDCl$_3$) δ 1.16 (t, J=7.3 Hz, 3H), 1.64-1.80 (m, 8H), 2.46 (s, 3H), 3.54 (q, J=7.3 Hz, 2H), 3.57 (s, 2H), 6.72 (s, 1H).

N-ethyl-2,3-diaza-spiro[4.4]non-3-ene-2-carboximidothioic acid methyl ester (compound 2)

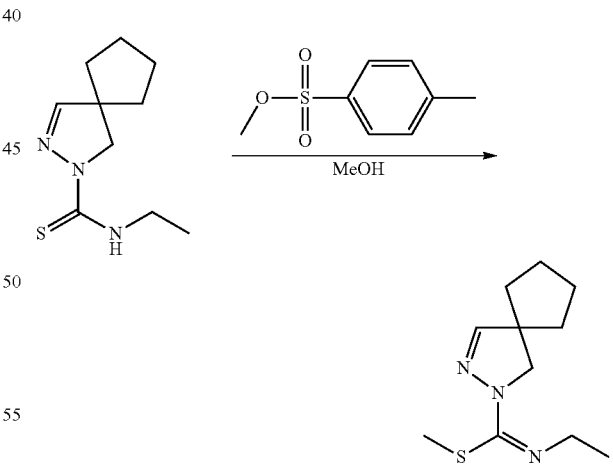

To a solution of 1.0 g (4.7 mmol) 2,3-diazaspiro[4.4]non-3-ene-2-carbothioic acid ethylamide in 10 mL methanol was added 1.1 g (5.7 mmol) methyl p-toluenesulfonate. The mixture was refluxed for 48 hrs and concentrated under reduced pressure. The residue was triturated with 30 mL diethyl ether and all volatiles were removed from the isolated oily product under reduced pressure. The residual oil was taken up in 40 mL dichloromethane and extracted 3 times with a saturated aqueous NaHCO$_3$ solution. The organic layer was dried over MgSO₄, filtered and evaporated to dryness under reduced pressure to afford 0.33 g (1.5 mmol, 31%) of N-ethyl-2,3-diaza-spiro[4.4]non-3-ene-2-carboximidothioic acid methyl ester as a light-brown oil. ¹H NMR identical to spectrum obtained from material prepared by using iodomethane as methylating agent (vide supra).

N-(4-{[(2,3-diaza-spiro[4.4]non-3-en-2-yl)-ethylamino-methylene]-sulfamoyl}-phenyl)-acetamide (compound 3 via novel route)

N-(4-{[(2,3-diaza-spiro[4.4]non-3-en-2-yl)-ethylamino-methylene]-sulfamoyl}-phenyl)-acetamide (compound 3 via route 2 disclosed in WO 2009/115515)

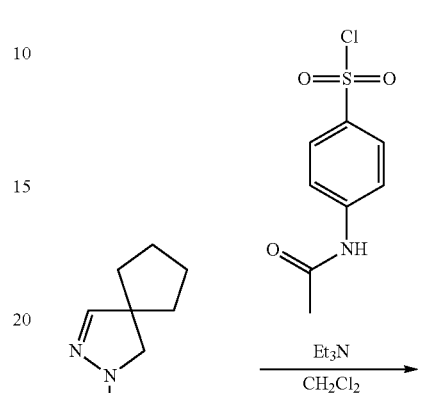

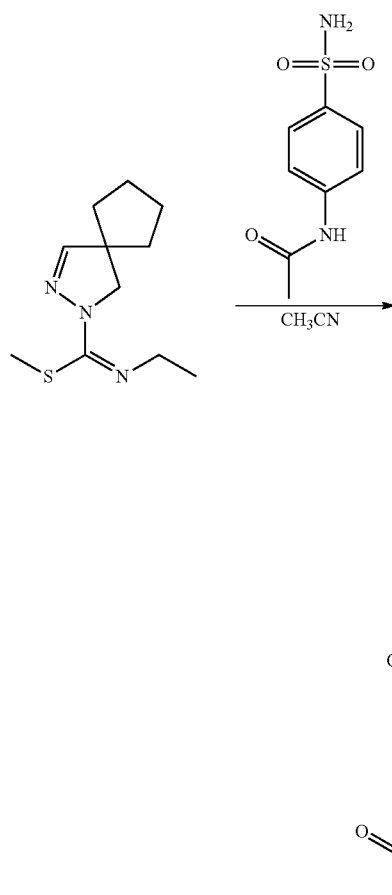

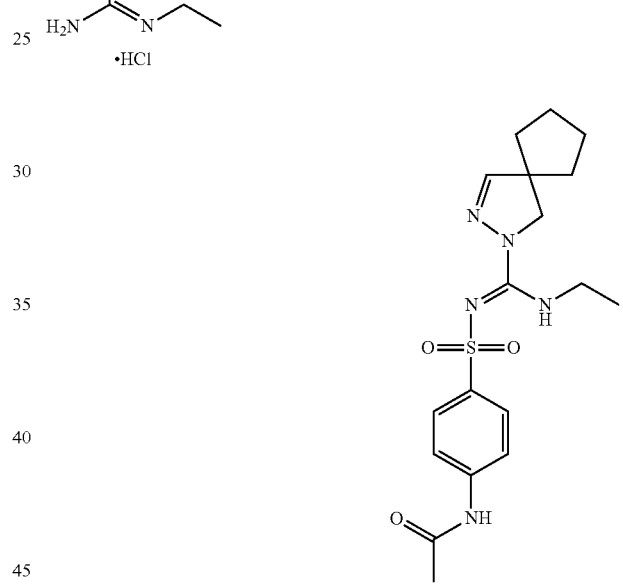

157 mg (1 mol equiv.) N-Ethyl-2,3-diaza-spiro[4.4]non-3-ene-2-carboximidothioic acid methyl ester and 157 mg (1.05 mol equiv.) 4-acetamidobenzenesulfonamide were taken up in 5 mL acetonitrile. The reaction mixture was refluxed overnight under magnetic stirring and volatiles were removed in vacuo. The residue was taken up in ethyl acetate and extracted with 2N NaOH. The organic layer was dried over Na₂SO₄, filtered and evaporated to dryness. Purification by flash chromatography on silica gel (ethyl acetate) afforded 236 mg (87%) of N-(4-{[(2,3-diaza-spiro[4.4]non-3-en-2-yl)-ethylamino-methylene]-sulfamoyl}-phenyl)-acetamide. ¹H NMR (400 MHz, CDCl₃) δ 1.14 (t, J=7.2 Hz, 3H), 1.62-1.83 (m, 8H), 2.20 (s, 3H), 3.43-3.51 (m, 2H), 3.80 (s, 2H), 6.80 (s, 1H), 6.87 (br.s., 1H), 7.56 (d, J=8.8 Hz, 2H), 7.77 (br.s., 1H), 7.83 (d, J=8.8 Hz, 2H).

N-Ethyl-2,3-diaza-spiro[4.4]non-3-ene-2-carboxamidine hydrochloride (60 g, 260.08 mmol; isolated from reaction of N-ethyl-2,3-diaza-spiro[4.4]non-3-ene-2-carboxamidine, synthesized as described in WO 2009/115515, with HCl in isopropanol) was dissolved in 1000 mL dichloromethane, and 4-acetylamino-benzenesulfonyl chloride (60.7 g, 260.08 mmol) was added. Under mechanical stirring, triethylamine (131.6 g, 1300.4 mmol) was added over a period of 20 minutes, and the mixture was stirred overnight at room temperature. The reaction mixture was extracted with water (250 mL) and the organic phase was concentrated under reduced pressure (40° C., 600 mbar). The oily residue was coevaporated twice with 96% ethanol (250 mL) and taken up in 500 mL dichloromethane. The organic phase was extracted with 1N aqueous HCl (75 mL) and subsequently twice with water (200 mL) and evaporated to dryness under reduced pressure to yield 78 g (199.2 mmol, 77%) of N-(4-{[(2,3-diaza-spiro[4.4]non-3-en-2-yl)-ethylamino-methylene]sulfamoyl}- phenyl)-acetamide. ¹H NMR identical to spectrum obtained from material prepared via novel route (vide supra).

4-Amino-N-[(2,3-diaza-spiro[4.4]non-3-en-2-yl)-ethylamino-methylene]-benzenesulfonamide (compound 4 from compound 3)

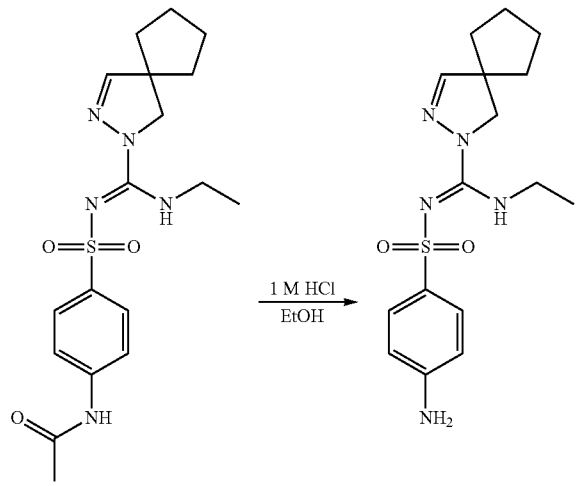

179 g N-(4-{[(2,3-diaza-spiro[4.4]non-3-en-2-yl)-ethylamino-methylene]sulfamoyl}-phenyl)acetamide was dissolved in 2685 mL EtOH, and 1370 mL of 1M HCl (3 mol equiv.) was added. The mixture was stirred at 55° C. for 45 h. and concentrated under reduced pressure. The residue was taken up in 2200 mL butyl acetate, and 3800 mL of 5% aqueous NaHCO$_3$ was dosed over a period of 55 minutes under stirring. The organic phase was separated and the aqueous phase was extracted with 200 mL butyl actetate. The combined organic layers were washed with 1300 mL water and evaporated to dryness to give 133 g of crude material. The residue was recrystallized from 800 mL of EtOH and dried in vacuo at 50° C. to give 87.8 g (55%) of 4-amino-N-[(2,3-diaza-spiro[4.4]non-3-en-2-yl)-ethylamino-methylene]-benzenesulfonamide. ¹H NMR (400 MHz, CDCl$_3$) δ 1.14 (t, J=7.22 Hz, 3H), 1.47-1.89 (m, 8H), 3.35-3.57 (m, 2H), 3.79 (s, 2H), 4.02 (br.s., 2H), 6.65 (d, J=8.73 Hz, 2H), 6.78 (s, 1H), 6.91 (br. s., 1H), 7.70 (d, J=8.73 Hz, 2H).

4,4-Dimethyl-4,5-dihydro-pyrazole-1-carbothioic acid ethylamide (compound 5)

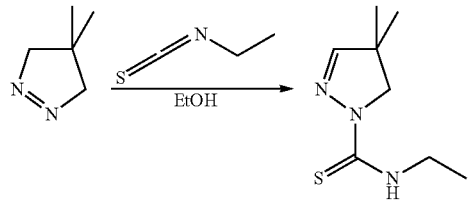

10 g (1 mol equiv.) 4,4-Dimethyl-4,5-dihydro-3H-pyrazole (synthesized as described in WO 2008/034863) and 11.6 mL (1.3 mol equiv.) ethyl isothiocyanate were added to 100 mL ethanol. The reaction mixture was refluxed for 1 hour. Silica gel was added and volatiles were removed in vacuo.

Purification by flash chromatography on silica gel (Et$_2$O: PA=1:2) afforded 15.2 g (80%) of 4,4-dimethyl-4,5-dihydro-pyrazole-1-carbothioic acid ethylamide. ¹H NMR (400 MHz, CDCl$_3$) δ 1.19-1.30 (m, 9H), 3.63-3.72 (m, 2H), 3.93 (s, 2H), 6.74 (s, 1H), 7.14 (br.s., 1H).

N-Ethyl-4,4-dimethyl-4,5-dihydro-pyrazole-1-carboximidothioic acid methyl ester (compound 6)

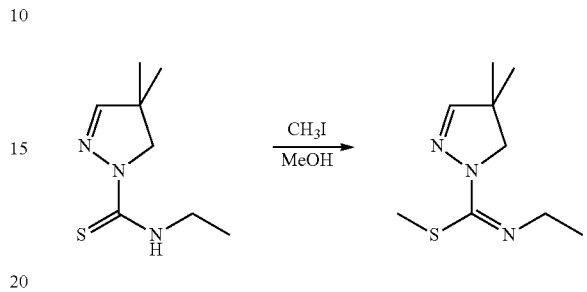

15 g (1 mol equiv.) 4,4-Dimethyl-4,5-dihydro-pyrazole-1-carbothioic acid ethylamide was dissolved in 300 mL methanol, 50.4 mL (10 mol equiv.) iodomethane was added and the reaction mixture was heated at 50° C. for 3 hours. Volatiles were removed in vacuo. The residue was taken up in DCM and extracted with 5% aqueous NaHCO$_3$. The organic layer was washed twice with water, dried over Na$_2$SO$_4$, filtered and evaporated to dryness to give 15.5 g (96%) N-ethyl-4,4-dimethyl-4,5-dihydro-pyrazole-1-carboximidothioic acid methyl ester. ¹H NMR (400 MHz, CDCl$_3$) δ 1.16 (t, J=7.3 Hz, 3H), 1.20 (s, 6H), 2.45 (s, 3H), 3.49 (s, 2H), 3.53 (q, J=7.3 Hz, 2H), 6.66 (s, 1H).

3-Chloro-N-[(4,4-dimethyl-4,5-dihydro-pyrazol-1-yl)-ethylamino-methylene]-benzenesulfonamide (compound 7)

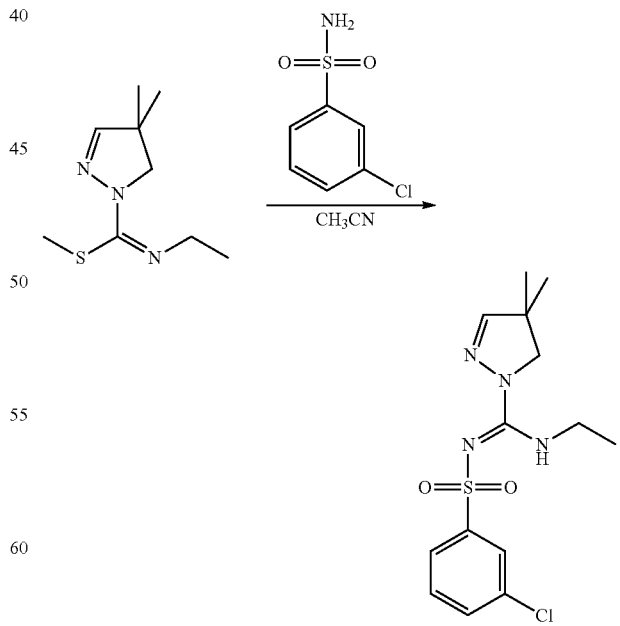

0.75 g (1 mol equiv.) N-Ethyl-4,4-dimethyl-4,5-dihydro-pyrazole-1-carboximidothioic acid methyl ester and 0.76 g (1.05 mol equiv.) 3-chlorobenzenesulfonamide were added to 10 mL acetonitrile. The reaction mixture was refluxed overnight and volatiles were removed in vacuo.

The residue was taken up in ethyl acetate and extracted with 2N NaOH. The organic layer was dried over $Na_2SO_4$, filtered and evaporated to dryness. Purification by flash chromatography on silica gel ($Et_2O$) afforded 1.26 g (98%) of 3-chloro-N-[(4,4-dimethyl-4,5-dihydro-pyrazol-1-yl)-ethylamino-methylene]-benzenesulfonamide. $^1$H NMR (400 MHz, $CDCl_3$) δ 1.17 (t, J=7.2 Hz, 3H), 1.23 (s, 6H), 3.43-3.52 (m, 2H), 3.79 (br.s., 2H), 6.77 (s, 1H), 6.60-6.90 (br.s., 1H), 7.37-7.42 (m, 1H), 7.43-7.47 (m, 1H), 7.81-7.85 (m, 1H), 7.94 (m, 1H).

3-Chloro-N-[(4,4-dimethyl-4,5-dihydro-pyrazol-1-yl)-ethylamino-methylene]-4-methoxy-benzenesulfonamide (compound 8)

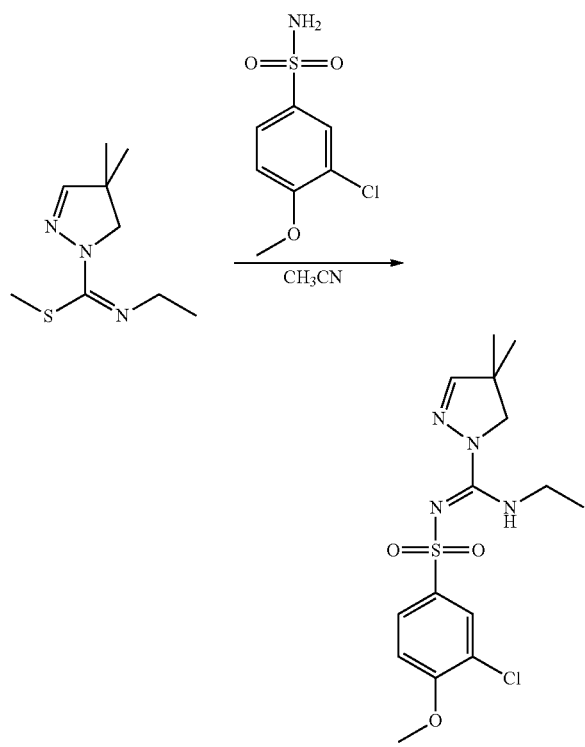

0.75 g (1 mol equiv.) N-Ethyl-4,4-dimethyl-4,5-dihydro-pyrazole-1-carboximidothioic acid methyl ester and 0.94 g (1.05 mol equiv.) 3-chloro-4-methoxy-benzenesulfonamide were added to 10 mL acetonitrile. The reaction mixture was refluxed overnight and volatiles were removed in vacuo. The residue was taken up in ethyl acetate and extracted with 2N NaOH. The organic layer was dried over $Na_2SO_4$, filtered and evaporated to dryness. Purification by flash chromatography on silica gel ($Et_2O$) afforded 1.43 g (97%) 3-chloro-N-[(4,4-dimethyl-4,5-dihydro-pyrazol-1-yl)-ethylamino-methylene]-4-methoxy-benzenesulfonamide. $^1$H NMR (400 MHz, $CDCl_3$) δ 1.17 (t, J=7.3 Hz, 3H), 1.22 (s, 6H), 3.43-3.52 (m, 2H), 3.77 (br.s., 2H), 3.95 (s, 3H), 6.75 (s, 1H), 6.96 (d, J=8.6 Hz, 1H), 6.70-6.90 (br.s., 1H) 7.82 (dd, J=8.6, 2.3 Hz, 1H), 7.95 (d, J=2.3 Hz, 1H).

3-Ethyl-4,5-dihydro-pyrazole-1-carbothioic acid ethylamide (compound 9)

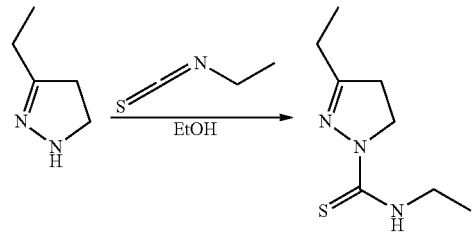

1.25 g (1 mol equiv.) 3-Ethyl-4,5-dihydro-1H-pyrazole (synthesized as described in WO 2008/034863) and 1.45 ml (1.3 mol equiv.) ethyl isothiocyanate were added to 10 mL ethanol. The reaction mixture was refluxed for 5 hours, silica gel was added and volatiles were removed in vacuo. Purification by flash chromatography on silica gel ($Et_2O$:PA=1:1) afforded 1.54 g (65%) 3-ethyl-4,5-dihydro-pyrazole-1-carbothioic acid ethylamide. $^1$H NMR (400 MHz, $CDCl_3$) δ 1.18 (t, J=7.5 Hz, 3H), 1.25 (t, J=7.2 Hz, 3H), 2.38 (q, J=7.5 Hz, 2H), 2.83 (t, J=9.9 Hz, 2H), 3.63-3.72 (m, 2H), 4.19 (t, J=9.9 Hz, 2H), 7.06 (br.s., 1H).

3,N-Diethyl-4,5-dihydro-pyrazole-1-carboximidothioic acid methyl ester (compound 10)

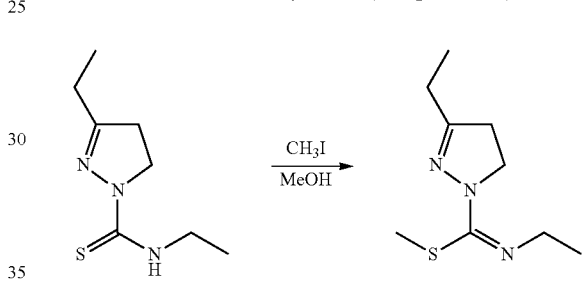

1.51 g (1 mol equiv.) 3-Ethyl-4,5-dihydro-pyrazole-1-carbothioic acid ethylamide was dissolved in 30 mL methanol, 5.1 mL (10 mol equiv.) iodomethane was added and the reaction mixture was heated at 50° C. for 1 hour. Volatiles were removed in vacuo. The residue was taken up in DCM and extracted with 5% aqueous $NaHCO_3$. The organic layer was washed twice with water, dried over $Na_2SO_4$, filtered and evaporated to dryness to give 1.44 g (89%) 3,N-diethyl-4,5-dihydro-pyrazole-1-carboximidothioic acid methyl ester. $^1$H NMR (400 MHz, $CDCl_3$) δ 1.12-1.21 (m, 6H), 2.39 (q, J=7.4 Hz, 2H), 2.48 (s, 3H), 2.70 (t, J=9.7 Hz, 2H), 3.52 (q, J=7.2 Hz, 2H), 3.75 (t, J=9.7 Hz, 2H).

2-Chloro-N-[ethylamino-(3-ethyl-4,5-dihydro-pyrazol-1-yl)-methylene]-benzenesulfonamide (compound 11)

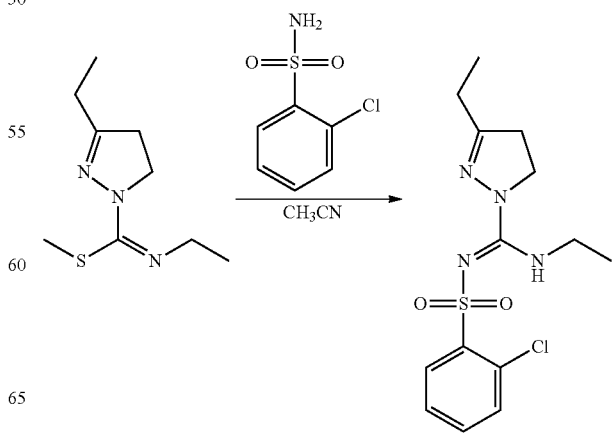

1.42 g (1 mol equiv.) 3,N-Diethyl-4,5-dihydro-pyrazole-1-carboximidothioic acid methyl ester and 1.43 g (1.05 mol equiv.) 2-chlorobenzenesulfonamide were added to 20 mL acetonitrile. The reaction mixture was refluxed overnight and volatiles were removed in vacuo. The residue was taken up in ethyl acetate and extracted with 2N NaOH. The organic layer was dried over $Na_2SO_4$, filtered and evaporated to dryness. The residue obtained after purification by flash chromatography on silica gel ($Et_2O$) was triturated with diisopropyl ether to afford 2.08 g (81%) 2-chloro-N-[ethylamino-(3-ethyl-4,5-dihydro-pyrazol-1-yl)-methylene]-benzenesulfonamide.
$^1$HNMR (400 MHz, $CDCl_3$) δ 1.15 (t, J=7.3 Hz, 3H), 1.17 (t, J=7.3 Hz, 3H), 2.38 (q, J=7.3 Hz, 2H), 2.80 (t, J=9.8 Hz, 2H), 3.44-3.53 (m, 2H), 4.11 (t, J=9.8 Hz, 2H), 6.73 (br.s., 1H), 7.33 (dt, J=7.6, 2.0 Hz, 1H), 7.38 (dt, J=7.6, 2.0 Hz, 1H), 7.46 (dd, J=7.6, 2.0 Hz, 1H), 8.17 (dd, J=7.6, 2.0 Hz, 1H).

N-(2-Bromo-phenyl)-2,2,2-trifluoro-acetamide (compound 12)

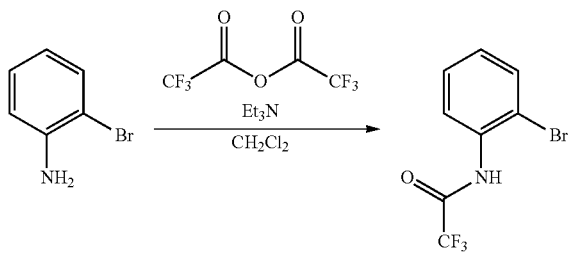

24.9 g (1 mol equiv.) 2-Bromoaniline was dissolved in 200 mL dichloromethane; 28 mL (1.4 mol equiv.) triethylamine was added, the reaction mixture was cooled to 0° C., and 24 mL (1.2 mol equiv.) trifluoroacetic anhydride was added dropwise (keeping the temperature of the reaction mixture below 10° C.). After the addition was complete, the mixture was warmed to room temperature and stirred for another 2 hours. The mixture was quenched with water and the organic layer was separated, dried over $Na_2SO_4$, filtered and evaporated under reduced pressure. Purification by flash chromatography on silica gel ($Et_2O$:PA=1:6) afforded 34.6 g (89%) N-(2-bromo-phenyl)-2,2,2-trifluoro-acetamide. $^1$H NMR (400 MHz, $CDCl_3$) δ 7.12 (dt, J=8.0, 1.3 Hz, 1H), 7.39 (dt, J=8.0, 1.3 Hz, 1H), 7.61 (dd, J=8.0, 1.3 Hz, 1H), 8.31 (dd, J=8.0, 1.3 Hz, 1H), 8.45 (br.s., 1H).

3-Bromo-4-(2,2,2-trifluoro-acetylamino)-benzene-sulfonyl chloride (compound 13)

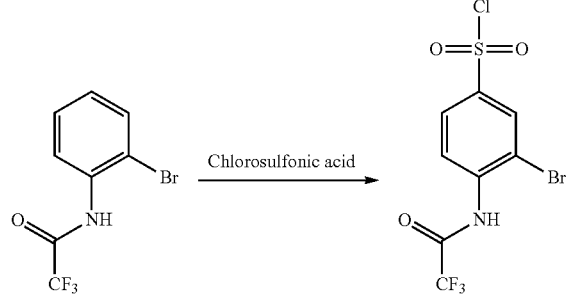 [SMILES: O=C(Nc1ccccc1Br)C(F)(F)F ; O=C(Nc1ccc(S(=O)(=O)Cl)cc1Br)C(F)(F)F]

15.0 g (1.0 equiv). N-(2-Bromo-phenyl)-2,2,2-trifluoro-acetamide was added in four portions to 18.7 mL (5 mol equiv.) chlorosulfonic acid under cooling in an ice-bath. The ice-bath was removed, the mixture was warmed to room temperature and subsequently to 80° C. After stirring for 1 hour the mixture was cooled to room temperature and poured into ice. It was extracted with dichloromethane, dried over $Na_2SO_4$, filtered and evaporated to dryness to give 17.4 g (85%) 3-bromo-4-(2,2,2-trifluoro-acetylamino)-benzene-sulfonyl chloride. $^1$H NMR (400 MHz, $CDCl_3$) δ 8.09 (dd, J=9.0, 2.0 Hz, 1H), 8.30 (d, J=2.0 Hz, 1H), 8.69 (d, J=9.0 Hz, 1H), 8.71 (br.s., 1H).

N-(2-Bromo-4-sulfamoyl-phenyl)-2,2,2-trifluoro-acetamide (compound 14)

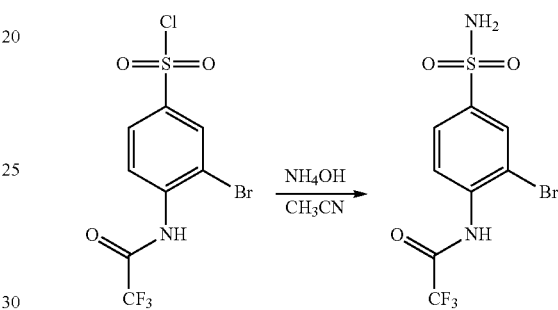

16.2 g (1 mol equiv.) 3-Bromo-4-(2,2,2-trifluoro-acetylamino)-benzenesulfonyl chloride was dissolved in 150 mL acetonitrile and cooled to 0° C. Dropwise, 20.8 mL (3 mol equiv.) ammoniumhydroxide was added and the reaction mixture was stirred at room temperature for 10 min. during which a white precipitate was formed. Volatiles were removed under reduced pressure, and the solid residue was washed with water and dried in vacuo to afford 14.3 g (94%) N-(2-bromo-4-sulfamoyl-phenyl)-2,2,2-trifluoro-acetamide.
$^1$H NMR (400 MHz, DMSO-$d_6$) δ 7.59 (s, 2H), 7.69 (d, J=8.2 Hz, 1H), 7.88 (dd, J=8.2, 1.8 Hz, 1H), 8.14 (d, J=1.8 Hz, 1H), 11.55 (s, 1H).

N-(2-Bromo-4-{[(4,4-dimethyl-4,5-dihydro-pyrazol-1-yl)-ethylamino-methylene]-sulfamoyl}-phenyl)-2,2,2-trifluoro-acetamide (compound 15)

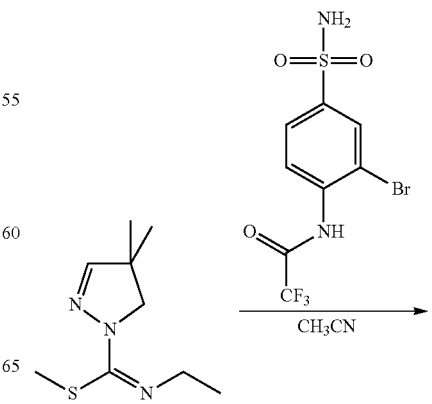

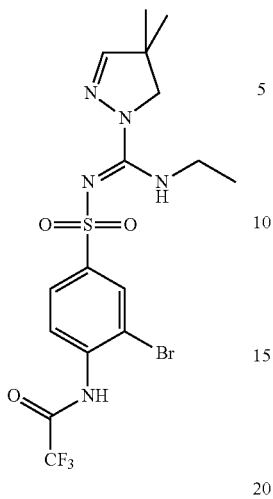

3.41 g (1 mol equiv.) N-Ethyl-4,4-dimethyl-4,5-dihydro-pyrazole-1-carboximidothioic acid methyl ester and 6.24 g (1.05 mol equiv.) N-(2-Bromo-4-sulfamoyl-phenyl)-2,2,2-trifluoro-acetamide were added to 100 mL acetonitrile. The reaction mixture was refluxed overnight, and subsequently volatiles were removed under reduced pressure. The residue was taken up in ethyl acetate and extracted with 2N NaOH, and the organic layer was dried over $Na_2SO_4$, filtered and evaporated to dryness. Purification by flash chromatography on silica gel ($Et_2O$) afforded 7.1 g (83%) N-(2-bromo-4-{[(4,4-dimethyl-4,5-dihydro-pyrazol-1-yl)-ethylamino-methylene]-sulfamoyl}-phenyl)-2,2,2-trifluoro-acetamide. $^1$H NMR (400 MHz, $CDCl_3$) δ 1.18 (t, J=7.3 Hz, 3H), 1.24 (s, 6H), 3.43-3.51 (m, 2H), 3.79 (br.s., 2H), 6.78 (s, 1H), 7.93 (dd, J=8.6, 2.0 Hz, 1H), 8.19 (d, J=2.0 Hz, 1H), 8.39 (d, J=8.6 Hz, 1H), 8.61 (br.s., 1H).

4-Amino-3-bromo-N-[(4,4-dimethyl-4,5-dihydro-pyrazol-1-yl)-ethylamino-methylene]benzene-sulfonamide (compound 16)

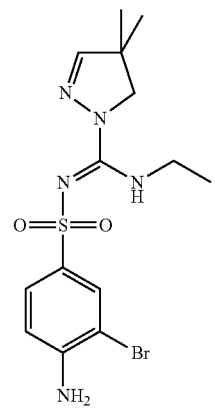

7.0 g (1 mol equiv.) N-(2-Bromo-4-{[(4,4-dimethyl-4,5-dihydro-pyrazol-1-yl)-ethylamino-methylene]-sulfamoyl}-phenyl)-2,2,2-trifluoro-acetamide was dissolved in 225 mL methanol; 10.3 g (5 mol equiv.) potassium carbonate and 30 mL water were added and the reaction mixture was refluxed for 2.5 hours. Volatiles were evaporated under reduced pressure, and the residue was taken up in ethyl acetate and extracted with 2N NaOH. The organic layer was dried over $Na_2SO_4$, filtered and concentrated on silica gel. Purification by flash chromatography on silica gel ($Et_2O$) afforded 4.1 g (73%) 4-amino-3-bromo-N-[(4,4-dimethyl-4,5-dihydro-pyrazol-1-yl)-ethylamino-methylene]-benzenesulfonamide. $^1$H NMR (400 MHz, $CDCl_3$) δ 1.17 (t, J=7.3 Hz, 3H), 1.21 (s, 6H), 3.43-3.52 (m, 2H), 3.74 (br.s., 2H), 4.45 (br.s., 2H), 6.73 (s, 1H), 6.75 (d, J=8.4 Hz, 1H), 6.83-6.92 (br.s., 1H), 7.65 (dd, J=8.4, 2.0 Hz, 1H), 7.99 (d, J=2.0 Hz, 1H).

2-Trifluoromethyl-1H-indole-5-sulfonic acid (4,4-dimethyl-4,5-dihydro-pyrazol-1-yl)-ethylamino-Methyleneamide (compound 17)

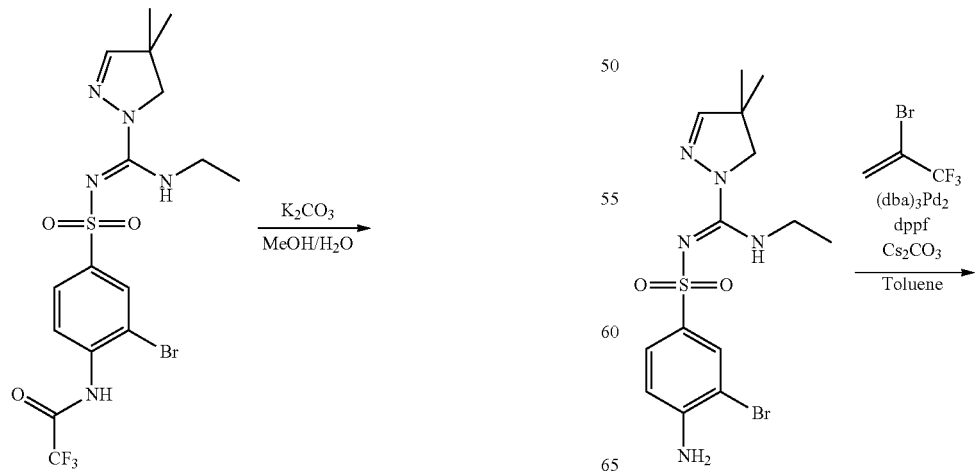

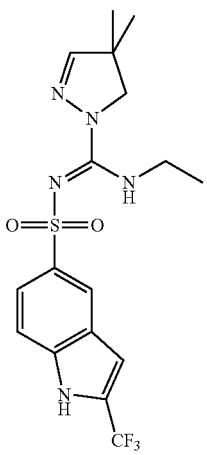

In a Pyrex bottle, purged with and kept under nitrogen, 2.23 g (1 mol equiv.) 4-amino-3-bromo-N-[(4,4-dimethyl-pyrazolidin-1-yl)-ethylamino-methylene]-benzenesulfonamide was dissolved in 33 mL degassed toluene. Subsequently, 2.54 g (0.5 mol equiv.) tris-(dibenzylidenaceton)-dipalladium(0), 4.61 g (1.5 mol equiv.) 1,1'-bis(diphenylphosphino)ferrocene, 2.17 g (1.2 mol equiv.) cesium carbonate and 1.94 g (2 mol equiv.) 2-bromo-3,3,3-trifluoropropene were added.

After a night at 115° C. the reaction mixture was cooled, ethyl acetate was added and the mixture was filtered over hyflo. Purification by flash chromatography on silica gel (Et$_2$O), followed by preparative TLC purification (Et$_2$O) afforded 254 mg (10%) 2-trifluoromethyl-1H-indole-5-sulfonic acid (4,4-dimethyl-4,5-dihydro-pyrazol-1-yl)-ethylamino-methyleneamide. $^1$H NMR (400 MHz, CDCl$_3$) δ 1.15 (t, J=7.3 Hz, 3H), 1.21 (s., 6H), 3.43-3.51 (m, 2H), 3.76 (br.s., 2H), 6.73 (s, 1H), 6.70-7.00 (br.s., 1H), 7.01 (s, 1H), 7.50 (d, J=8.7 Hz, 1H), 7.88 (dd, J=8.7, 1.5 Hz, 1H), 8.31 (br.s., 1H), 9.39 (br.s., 1H).

5-Thiophen-3-yl-4,5-dihydro-pyrazole-1-carbothioic acid ethylamide (compound 18)

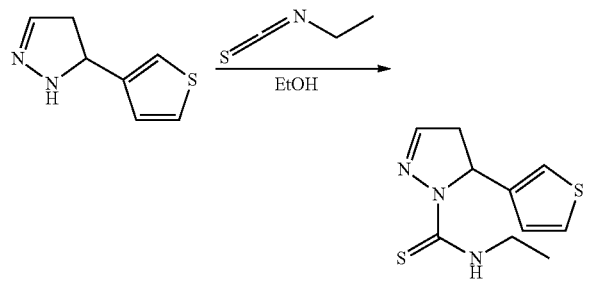

1.82 g (1 mol equiv.) 5-Thiophen-3-yl-4,5-dihydro-1H-pyrazole (synthesized as described in WO 2008/034863) and 1.36 mL (1.3 mol equiv.) ethyl isothiocyanate were added to 15 mL ethanol. The reaction mixture was refluxed for 5 hours, and subsequently concentrated on silica gel under reduced pressure. Purification by flash chromatography on silica gel (Et$_2$O:PA=1:1) afforded 0.70 g (26%) 5-thiophen-3-yl-4,5-dihydro-pyrazole-1-carbothioic acid ethylamide. $^1$H NMR (400 MHz, CDCl$_3$) δ 1.24 (t, J=7.2 Hz, 3H), 2.86 (ddd, J=18.5, 3.3, 1.7 Hz, 1H), 3.39 (ddd, J=18.5, 11.4, 1.7 Hz, 1H), 3.56-3.77 (m, 2H), 6.01 (dd, J=11.4, 3.3 Hz, 1H), 6.93 (dd, J=5.0, 1.0 Hz, 1H), 7.02 (t, J=1.7 Hz, 1H), 7.13 (m, 1H), 7.26 (m, 1H).

N-Ethyl-5-thiophen-3-yl-4,5-dihydro-pyrazole-1-carboximidothioic acid methyl ester (compound 19)

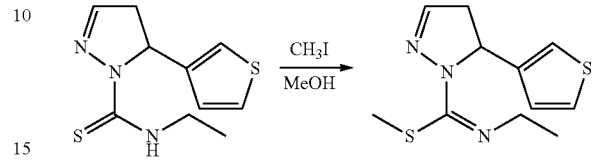

0.70 g (1 mol equiv.) 5-Thiophen-3-yl-4,5-dihydro-pyrazole-1-carbothioic acid ethylamide was dissolved in 14 mL methanol, 1.82 mL (10 mol equiv.) iodomethane was added and the reaction mixture was heated at 50° C. for 1 hour. Volatiles were removed in vacuo, the residue was taken up in dichloromethane and extracted with 5% aqueous NaHCO$_3$. The organic layer was washed twice with water, dried over Na$_2$SO$_4$, filtered and evaporated to dryness. Purification by flash chromatography on silica gel (EtOAc:MeOH=9:1) afforded 0.48 g (64%) N-ethyl-5-thiophen-3-yl-4,5-dihydro-pyrazole-1-carboximidothioic acid methyl ester. $^1$H NMR (400 MHz, CDCl$_3$) δ 1.03 (t, J=7.3, 3H), 2.44 (s, 3H), 2.84 (ddd, J=18.1, 10.4, 1.5 Hz, 1H), 3.23-3.51 (m, 3H), 5.57 (t, J=10.4 Hz, 1H), 6.87 (br.s., 1H), 7.00 (d, J=4.8, 1H), 7.13 (d, J=3.0, 1H), 7.24 (dd, J=4.8, 3.0 Hz, 1H).

3-Chloro-N-[ethylamino-(5-thiophen-3-yl-4,5-dihydro-pyrazol-1-yl)-methylene]-benzene-sulfonamide (compound 20)

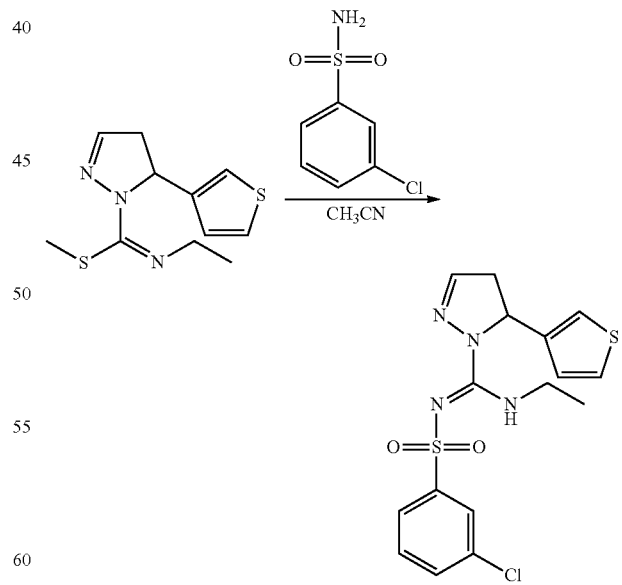

0.47 g (1 mol equiv.) N-Ethyl-5-thiophen-3-yl-4,5-dihydro-pyrazole-1-carboximidothioic acid methyl ester and 0.37 g (1.05 mol equiv.) 3-chlorobenzenesulfonamide were added to 7 mL acetonitrile. The reaction mixture was refluxed overnight and volatiles were removed under reduced pressure.

The residue was taken up in ethyl acetate and extracted with 2N NaOH. The organic layer was dried over Na$_2$SO$_4$, filtered and evaporated to dryness. Purification by flash chromatography on silica gel (Et$_2$O) afforded 0.44 g (49%) 3-chloro-N-[ethylamino-(5-thiophen-3-yl-4,5-dihydro-pyrazol-1-yl)-methylene]-benzenesulfonamide. $^1$H NMR (400 MHz, CDCl$_3$) δ 1.19 (t, J=7.2, 3H), 2.78 (ddd, J=18.6, 6.0, 1.4 Hz, 1H), 3.31 (ddd, J=18.6, 11.8, 1.4 Hz, 1H), 3.54-3.70 (m, 2H), 5.62 (dd, J=11.8, 6.0 Hz, 1H), 6.75 (d, J=4.3 Hz, 1H), 6.92 (d, J=2.0 Hz, 1H), 7.02 (br.s., 1H), 7.17-7.23 (m, 2H), 7.36 (m, 2H), 7.54 (br.s., 1H).

6-Chloro-imidazo[2,1-b]thiazole-5-sulfonic acid amide (compound 21)

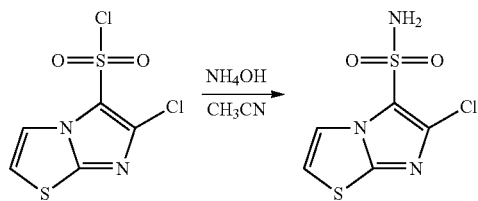

2 g (1 mol equiv.) 6-Chloro-imidazo[2,1-b]thiazole-5-sulfonyl chloride was dissolved in 20 mL acetonitrile and cooled to 0° C. Dropwise, 3.7 mL (3 mol equiv.) ammoniumhydroxide was added and the reaction mixture was stirred at room temperature for 10 min, during which a white precipitate was formed. Volatiles were removed under reduced pressure, and the solid residue was washed with water and dried in vacuo affording 1.62 g (88%) 6-chloro-imidazo[2,1-b]thiazole-5-sulfonic acid amide. $^1$H NMR (400 MHz, DMSO-d$_6$) δ 7.62 (d, J=4.6 1H), 7.98 (d, J=4.6 Hz, 1H), 8.00 (br.s., 2H).

8-Oxa-2,3-diaza-spiro[4.5]dec-3-ene-2-carbothioic acid methylamide (compound 22)

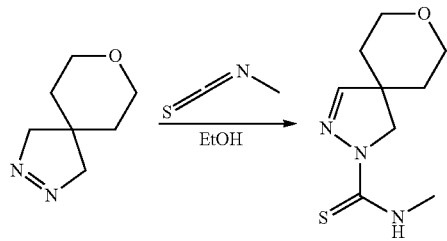

0.8 g (1 mol equiv.) 8-Oxa-2,3-diaza-spiro[4.5]dec-2-ene (synthesized as described in WO 2008/034863) and 0.54 g (1.3 mol equiv.) methyl isothiocyanate were added to 10 mL ethanol, and the reaction mixture was refluxed for 5 hours. Silica gel was added and volatiles were removed under reduced pressure. Purification by flash chromatography on silica gel (Et$_2$O) afforded 0.52 g (35%) 8-oxa-2,3-diaza-spiro[4.5]dec-3-ene-2-carbothioic acid methylamide. $^1$H NMR (400 MHz, CDCl$_3$) δ 1.52-1.59 (m, 3H), 1.82-1.90 (m, 2H), 3.17 (d, J=5.0, 3H), 3.56-3.64 (m, 2H), 3.86-3.92 (m, 2H), 4.11 (s, 2H), 6.80 (s, 1H), 7.21 (br.s., 1H).

N-Methyl-8-oxa-2,3-diaza-spiro[4.5]dec-3-ene-2-carboximidothioic acid methyl ester (comp. 23)

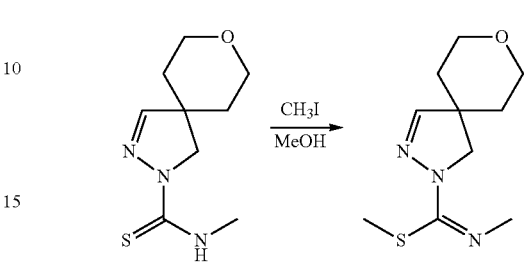

0.50 g (1 mol equiv.) 8-Oxa-2,3-diaza-spiro[4.5]dec-3-ene-2-carbothioic acid methylamide was dissolved in 10 mL methanol; 1.2 mL (10 mol equiv.) iodomethane was added and the reaction mixture was heated at 50° C. for 5 hours. Volatiles were removed under reduced pressure, and the residue was taken up in DCM and extracted with 5% aqueous NaHCO$_3$. The organic layer was washed twice with water, dried over Na$_2$SO$_4$, filtered and evaporated to dryness to yield 0.43 g (99%) N-methyl-8-oxa-2,3-diaza-spiro[4.5]dec-3-ene-2-carboximidothioic acid methyl ester. $^1$H NMR (400 MHz, CDCl$_3$) δ 1.53-1.60 (m, 2H), 1.80-1.88 (m, 2H), 2.47 (s, 3H), 3.26 (s, 3H), 3.56-3.64 (m, 2H), 3.68 (s, 2H), 3.83-3.89 (m, 2H), 6.73 (s, 1H).

6-Chloro-imidazo[2,1-b]thiazole-5-sulfonic acid methylamino-(8-oxa-2,3-diaza-spiro[4.5]dec-3-en-2-yl)-methyleneamide (compound 24)

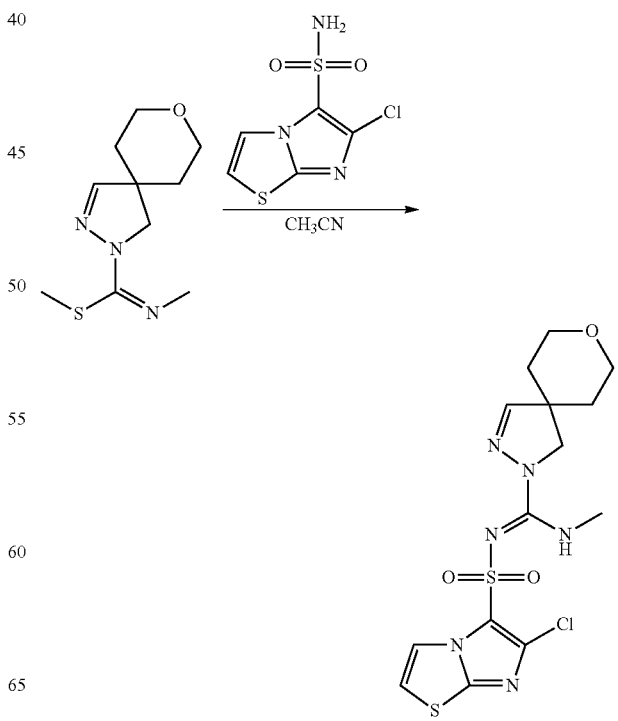

0.42 g (1 mol equiv.) N-Methyl-8-oxa-2,3-diaza-spiro[4.5]dec-3-ene-2-carboximidothioic acid methyl ester and 0.46 g (1.05 mol equiv.) 6-chloro-imidazo[2,1-b]thiazole-5-sulfonic acid amide were added to 7 mL acetonitrile and the reaction mixture was refluxed overnight. Volatiles were removed under reduced pressure, and the residue was taken up in ethylacetate and extracted with 2N NaOH. The organic layer was dried over $Na_2SO_4$, filtered and evaporated to dryness. Purification by flash chromatography on silica gel (EtOAc) afforded 0.56 g (69%) 6-chloro-imidazo[2,1-b]thiazole-5-sulfonic acid methylamino-(8-oxa-2,3-diaza-spiro[4.5]dec-3-en-2-yl)-methylene-amide. $^1$H NMR (400 MHz, $CDCl_3$) δ 1.51-1.57 (m, 2H), 1.80-1.89 (m, 2H), 3.10 (d, J=5.0 Hz, 3H), 3.51-3.59 (m, 2H), 3.83-3.90 (m, 4H), 3.89 (s, 2H), 6.89 (s, 1H), 6.99 (d, J=4.6 Hz, 1H), 7.12 (br.s., 1H), 8.01 (d, J=4.6 Hz, 1H).

4-Ethyl-4,5-dihydro-pyrazole-1-carbothioic acid ethylamide (compound 25)

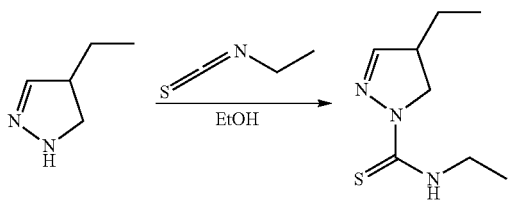

2.68 g (1 mol equiv.) 4-Ethyl-4,5-dihydro-1H-pyrazole (synthesized as described in WO 2008/034863) and 3.11 mL (1.3 mol equiv.) ethyl isothiocyanate were added to 20 mL ethanol. The reaction mixture was refluxed overnight, silica gel was added and volatiles were removed under reduced pressure. Purification by flash chromatography on silica gel ($Et_2O$:PA=1:3) afforded 1.80 g (36%) 4-ethyl-4,5-dihydro-pyrazole-1-carbothioic acid ethylamide. $^1$H NMR (400 MHz, $CDCl_3$) δ 0.99 (t, J=7.5 Hz, 3H), 1.25 (t, J=7.2 Hz, 3H), 1.47-1.71 (m, 2H), 3.08-3.18 (m, 1H), 3.63-3.72 (m, 2H), 3.86 (dd, J=11.5, 7.1 Hz, 1H), 4.25 (t, J=11.5 Hz, 1H), 6.90 (d, J=1.5 Hz, 1H), 7.12 (br.s., 1H).

4,N-Diethyl-4,5-dihydro-pyrazole-1-carboximidothioic acid methyl ester (compound 26)

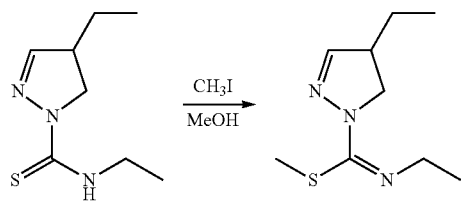

1.80 g (1 mol equiv.) 4-Ethyl-4,5-dihydro-pyrazole-1-carbothioic acid ethylamide was dissolved in 36 mL methanol; 6.1 mL (10 mol equiv.) iodomethane was added and the reaction mixture was heated at 50° C. for 4 hours. Volatiles were removed under reduced pressure, and the residue was taken up in DCM and extracted with 5% aqueous $NaHCO_3$. The organic layer was washed twice with water, dried over $Na_2SO_4$, filtered and evaporated to dryness to yield 1.68 g (87%) 4,N-diethyl-4,5-dihydro-pyrazole-1-carboximidothioic acid methyl ester. $^1$H NMR (400 MHz, $CDCl_3$) δ 0.98 (t, J=7.5 Hz, 3H), 1.16 (t, J=7.3 Hz, 3H), 1.45-1.70 (m, 2H), 2.45 (s, 3H), 2.97-3.07 (m, 1H), 3.44 (dd, J=11.0, 8.3 Hz, 1H), 3.51-3.58 (m, 2H), 3.83 (t, J=11.0 Hz, 1H), 6.81 (s, 1H).

Piperidine-1-sulfonic acid ethylamino-(4-ethyl-4,5-dihydro-pyrazol-1-yl)-methyleneamide (compound 27)

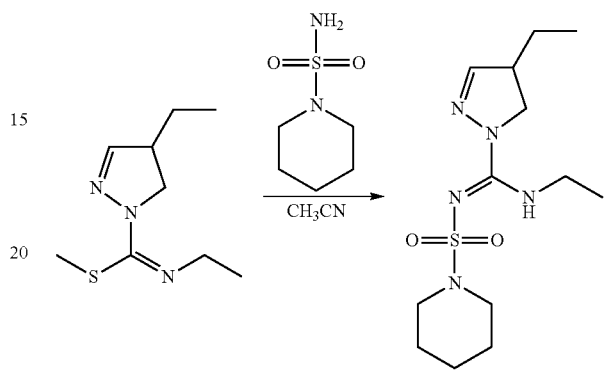

0.70 g (1 mol equiv.) 4,N-Diethyl-4,5-dihydro-pyrazole-1-carboximidothioic acid methyl ester and 0.61 g (1.05 mol equiv.) piperidine-1-sulfonic acid amide were added to 7 mL acetonitrile, and the reaction mixture was refluxed overnight. Volatiles were removed under reduced pressure, and the residue was taken up in ethyl acetate and extracted with 2N NaOH. The organic layer was dried over $Na_2SO_4$, filtered and evaporated to dryness. Purification by flash chromatography on silica gel ($Et_2O$:PA=2:1) afforded 1.12 g (96%) piperidine-1-sulfonic acid ethylamino-(4-ethyl-4,5-dihydro-pyrazol-1-yl)-methyleneamide. $^1$H NMR (400 MHz, $CDCl_3$) δ 0.99 (t, J=7.5 Hz, 3H), 1.21 (t, J=7.2 Hz, 3H), 1.45-1.72 (m, 8H), 3.07-3.17 (m, 5H), 3.48-3.57 (m, 2H), 3.73 (dd, J=11.0, 7.7 Hz, 1H), 4.08-4.19 (m, 1H), 6.58 (br.s., 1H), 6.87 (d, J=1.3 Hz, 1H)

Trans-2-phenyl-ethenesulfonic acid amide (compound 28)

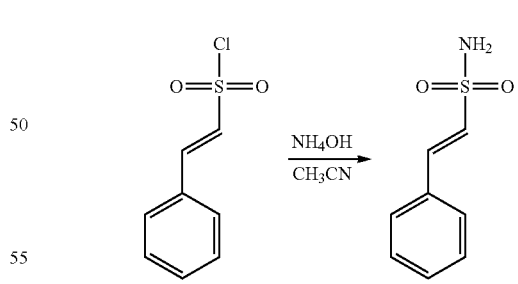

3.3 g (1 mol equiv.) Trans-2-phenyl-ethenesulfonyl chloride was dissolved in 33 mL acetonitrile and cooled to 0° C. Dropwise, 7.7 mL (3 eq) ammoniumhydroxide was added and the reaction mixture was stirred at room temperature for 10 min. Volatiles were removed under reduced pressure, and the solid residue was washed with water and dried in vacuo to afford 1.13 g (38%) trans-2-phenyl-ethenesulfonic acid amide. $^1$H NMR (400 MHz, DMSO-$d_6$) δ 7.11 (br.s., 2H), 7.23 (d, J=16.0 Hz, 1H), 7.31 (d, J=16.0 Hz, 1H), 7.41-7.45 (m, 3H), 7.64-7.71 (m, 2H).

Trans-2-phenyl-ethenesulfonic acid ethylamino-(4-ethyl-4,5-dihydro-pyrazol-1-yl)-methylene-amide (compound 29)

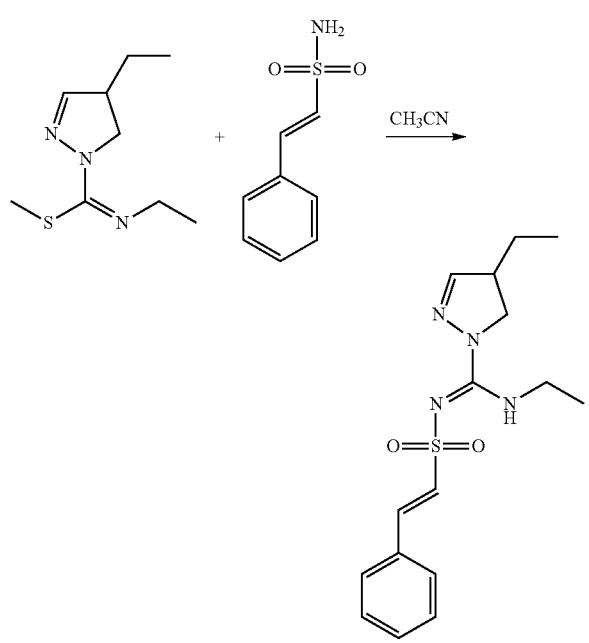

0.70 g (1 mol equiv.) 4,N-Diethyl-4,5-dihydro-pyrazole-1-carboximidothioic acid methyl ester and 0.68 g (1.05 mol equiv.) trans-2-phenyl-ethenesulfonic acid amide were added to 7 mL acetonitrile, and the reaction mixture was refluxed overnight. Volatiles were removed under reduced pressure, and the residue was taken up in ethyl acetate and extracted with 2N NaOH. The organic layer was dried over $Na_2SO_4$, filtered and evaporated to dryness. Purification by flash chromatography on silica gel ($Et_2O:PA=2:1$) afforded 1.00 g (81%) trans-2-phenyl-ethenesulfonic acid ethylamino-(4-ethyl-4,5-dihydro-pyrazol-1-yl)-methyleneamide. $^1H$ NMR (400 MHz, $CDCl_3$) δ 0.98 (t, J=7.5 Hz, 3H), 1.21 (t, J=7.2 Hz, 3H), 1.46-1.70 (m, 2H), 3.06-3.16 (m, 1H), 3.51-3.59 (m, 2H), 3.74 (dd, J=11.3, 7.5 Hz, 1H), 4.13 (t, J=11.3 Hz, 1H), 6.70-6.92 (m, 1H), 6.92 (d, J=1.3 Hz, 1H), 6.97 (d, J=15.4 Hz, 1H), 7.35-7.41 (m, 3H), 7.44 (d, J=15.4 Hz, 1H), 7.46-7.50 (m, 2H).

5-Chloro-thiophene-2-sulfonic acid amide (compound 30)

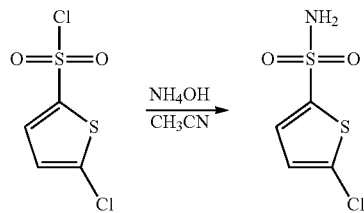

3 g (1 mol equiv.) 5-Chloro-thiophene-2-sulfonyl chloride was dissolved in 30 mL acetonitrile and cooled to 0° C. Dropwise, 6.5 mL (3 mol equiv.) ammoniumhydroxide was added and the reaction mixture was stirred at room temperature for 10 min. Volatiles were removed under reduced pressure, and the solid residue was washed with water and dried in vacuo to afford 2.49 g (91%) 5-chloro-thiophene-2-sulfonic acid amide. $^1H$ NMR (400 MHz, DMSO-$d_6$) δ 7.21 (d, J=4.0 Hz, 1H), 7.43 (d, J=4.0 Hz, 1H), 7.79 (br.s., 2H).

4,4-Dimethyl-4,5-dihydro-pyrazole-1-carbothioic acid amide (compound 31)

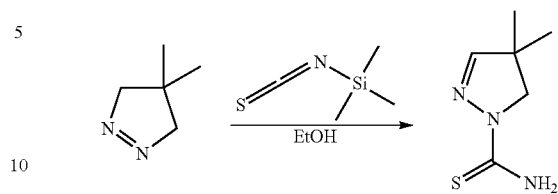

3.0 g (1 mol equiv.) 4,4-Dimethyl-4,5-dihydro-3H-pyrazole (synthesized as described in WO 2008/034863) and 5.6 mL (1.3 mol equiv.) trimethylsilyl isothiocyanate were added to 30 mL ethanol and the reaction mixture was refluxed for 5 hours. Silica gel was added and volatiles were removed under reduced pressure. Purification by flash chromatography on silica gel ($Et_2O:PA=2:1$) afforded 3.91 g (81%) 4,4-dimethyl-4,5-dihydro-pyrazole-1-carbothioic acid amide. $^1H$ NMR (400 MHz, $CDCl_3$) δ 1.27 (s, 6H), 3.94 (s, 2H), 5.82-6.34 (br.s., 1H), 6.50-7.00 (br.s., 1H), 6.80 (s, 1H).

4,4-Dimethyl-4,5-dihydro-pyrazole-1-carboximidothioic acid methyl ester (compound 32)

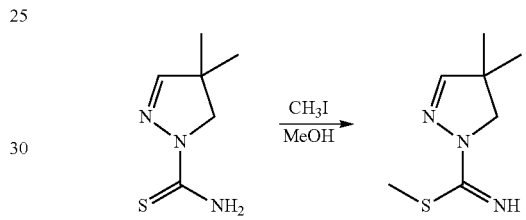

1.50 g (1 mol equiv.) 4,4-Dimethyl-4,5-dihydro-pyrazole-1-carbothioic acid amide was dissolved in 30 ml methanol; 5.9 mL (10 mol equiv.) iodomethane was added and the reaction mixture was stirred at room temperature for 2 hours. Volatiles were removed under reduced pressure, and the residue was taken up in DCM and extracted with 5% aqueous $NaHCO_3$. The organic layer was washed twice with water, dried over $Na_2SO_4$, filtered and evaporated to dryness, yielding 1.53 g (94%) 4,4-dimethyl-4,5-dihydro-pyrazole-1-carboximidothioic acid methyl ester. $^1H$ NMR (400 MHz, $CDCl_3$) δ 1.24 (s, 6H), 2.32 (s, 3H), 3.65 (s, 2H), 6.63 (s, 1H), 6.66-6.85 (br.s., 1H).

5-Chloro-thiophene-2-sulfonic acid amino-(4,4-dimethyl-4,5-dihydro-pyrazol-1-yl)-methylene-amide (compound 33)

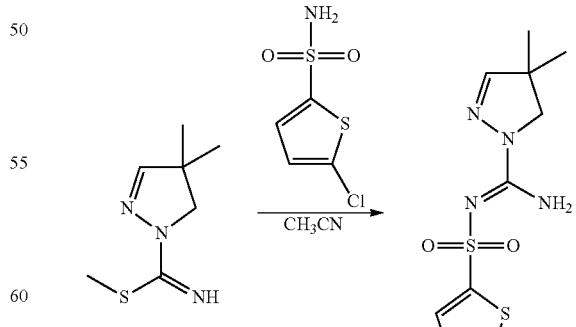

1.0 g (1 mol equiv.) 4,4-Dimethyl-4,5-dihydro-pyrazole-1-carboximidothioic acid methyl ester and 1.21 g (1.05 mol equiv.) 5-chloro-thiophene-2-sulfonic acid amide were added to 10 mL acetonitrile. The reaction mixture was refluxed overnight, and volatiles were removed under reduced pressure. The residue was taken up in ethyl acetate and extracted with 2N NaOH. The organic layer was dried over $Na_2SO_4$, filtered and evaporated to dryness. Purification by flash chromatography on silica gel ($Et_2O$:PA=2:1) afforded 1.58 g (80%) 5-chloro-thiophene-2-sulfonic acid amino-(4,4-dimethyl-4,5-dihydro-pyrazol-1-yl)-methyleneamide. $^1$H NMR (400 MHz, $CDCl_3$) δ 1.25 (s, 6H), 3.63 (s, 2H), 6.00-6.50 (br.s., 1H), 6.79 (s, 1H), 6.85 (d, J=4.0 Hz, 1H), 7.10-7.35 (br.s., 1H), 7.37 (d, J=4.0 Hz, 1H).

4-Ethyl-4,5-dihydro-pyrazole-1-carbothioic acid (2,2,2-trifluoro-ethyl)-amide (compound 34)

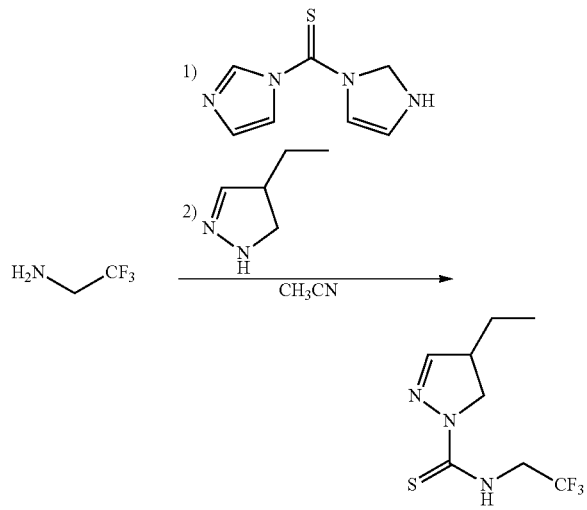

A solution of 3.2 mL (1 mol equiv.) 2,2,2-trifluoro-ethylamine in 60 mL acetonitrile was added to a stirred solution of 7.4 g (2.1 mol equiv.) 1,1'-thiocarbonyldiimidazole in 100 mL acetonitrile at room temperature. The reaction mixture was stirred overnight, and 1.96 g (1 mol equiv.) 4-Ethyl-4,5-dihydro-1H-pyrazole (synthesized as described in WO 2008/034863) was added to the reaction mixture. After 1 hour volatiles were removed under reduced pressure and the residue was purified by flash chromatography on silica gel ($Et_2O$:PA=1:3) to afford 2.85 g (60%) 4-ethyl-4,5-dihydro-pyrazole-1-carbothioic acid (2,2,2-trifluoro-ethyl)-amide. $^1$H NMR (400 MHz, $CDCl_3$) δ 1.01 (t, J=7.5 Hz, 3H), 1.50-1.74 (m, 2H), 3.13-3.23 (m, 1H), 3.86 (dd, J=11.6, 7.1 Hz, 1H), 4.27 (t, J=11.6 Hz, 1H), 4.44 (m, 2H) 6.99 (d, J=1.5 Hz, 1H), 7.32-7.40 (br.s., 1H).

4-Ethyl-N-(2,2,2-trifluoro-ethyl)-4,5-dihydro-pyrazole-1-carboximidothioic acid methyl ester (compound 35)

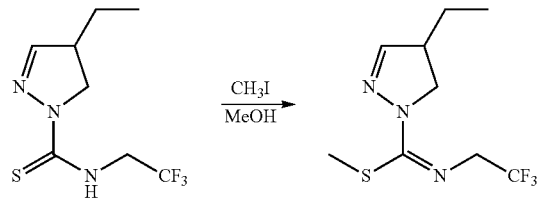 [SMILES: "MeOH" ; CCC1C=NN(C(=S)NCC(F)(F)F)C1 ; "CH3I" ; CCC1C=NN(/C(=N\CC(F)(F)F)SC)C1]

2.80 g (1 mol equiv.) 4-Ethyl-4,5-dihydro-pyrazole-1-carbothioic acid (2,2,2-trifluoro-ethyl)-amide was dissolved in 56 mL methanol; 7.3 mL (10 mol equiv.) iodomethane was added and the reaction mixture was heated at 50° C. for 4 hours. Volatiles were removed under reduced pressure, and the residue was taken up in DCM and extracted with 5% aqueous $NaHCO_3$. The organic layer was washed twice with water, dried over $Na_2SO_4$, filtered and evaporated to dryness. Purification by flash chromatography on silica gel ($Et_2O$:PA=1:1) afforded 0.57 g (19%) 4-ethyl-N-(2,2,2-trifluoro-ethyl)-4,5-dihydro-pyrazole-1-carboximidothioic acid methyl ester. $^1$H NMR (400 MHz, $CDCl_3$) δ 0.99 (t, J=7.5 Hz, 3H), 1.46-1.70 (m, 2H), 2.48 (s, 3H), 3.01-3.11 (m, 1H), 3.50 (dd, J=11.5, 7.8 Hz, 1H), 3.90 (t, J=11.5 Hz, 1H), 3.99-4.11 (m, 2H), 6.85 (d, J=1.5 Hz, 1H).

3-Chloro-N-[(4-ethyl-4,5-dihydro-pyrazol-1-yl)-(2,2,2-trifluoro-ethylamino)-methylene]-benzene-sulfonamide (compound 36)

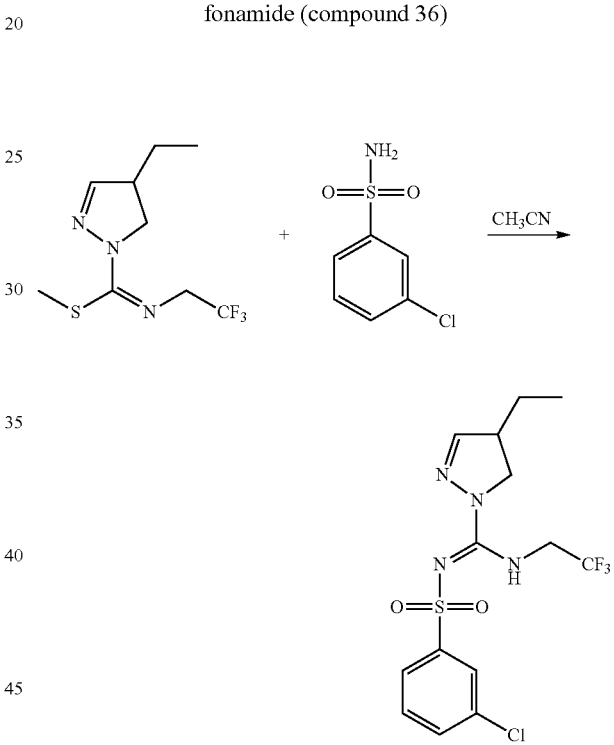

0.57 g (1 mol equiv.) 4-Ethyl-N-(2,2,2-trifluoro-ethyl)-4,5-dihydro-pyrazole-1-carboximidothioic acid methyl ester and 3.0 g (6.8 mol equiv.) 3-chloro-benzenesulfonamide were added to 20 mL acetonitrile. The reaction mixture was refluxed for 72 hours, and volatiles were removed under reduced pressure. The residue was taken up in ethyl acetate and extracted with 2N NaOH. The organic layer was dried over $Na_2SO_4$, filtered and evaporated to dryness. Purification by flash chromatography on silica gel ($Et_2O$:PA=1:1) afforded 0.36 g (38%) 3-chloro-N-[(4-ethyl-4,5-dihydro-pyrazol-1-yl)-(2,2,2-trifluoro-ethylamino)-methylene]-benzenesulfonamide. $^1$H NMR (400 MHz, $CDCl_3$) δ 1.00 (t, J=7.5 Hz, 3H), 1.51-1.74 (m, 2H), 3.16-3.27 (m, 1H), 3.87 (dd, J=11.2, 7.5 Hz, 1H), 4.03-4.14 (m, 2H), 4.28 (t, J=11.2 Hz, 1H), 7.03 (d, J=1.5 Hz, 1H), 7.41 (t, J=7.8 Hz, 1H), 7.46-7.50 (m, 1H), 7.79-7.84 (m, 1H), 7.91-7.94 (m, 1H).

4-Amino-N-[(4,4-dimethyl-4,5-dihydro-pyrazol-1-yl)-ethylamino-methylene]-benzenesulfonamide (Compound 37)

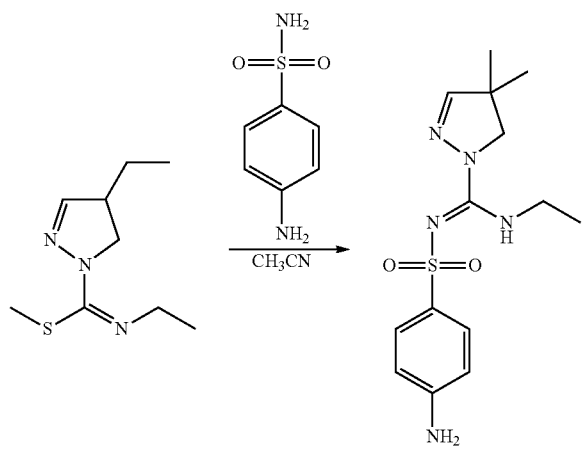

0.75 g (1 mol equiv.) N-Ethyl-4,4-dimethyl-4,5-dihydro-pyrazole-1-carboximidothioic acid methyl ester and 0.65 g (1.0 mol equiv.) sulfanilamide were added to 10 mL acetonitrile. The reaction mixture was refluxed overnight, and volatiles were removed under reduced pressure. The residue was taken up in ethyl acetate and extracted with 2N NaOH. The organic layer was dried over $Na_2SO_4$, filtered and evaporated to dryness. Purification by flash chromatography on silica gel ($Et_2O$:EtOAc=1:1) afforded 1.13 g (86%) 4-amino-N-[(4,4-dimethyl-4,5-dihydro-pyrazol-1-yl)-ethylamino-methylene]-benzenesulfonamide. $^1$H NMR (400 MHz, $CDCl_3$) δ 1.15 (t, J=7.2 Hz, 3H), 1.20 (s, 6H), 3.43-3.51 (m, 2H), 3.74 (br.s., 2H), 3.98 (br.s., 2H), 6.66 (d, J=8.6 Hz, 2H), 6.71 (s, 1H), 7.71 (d, J=8.6 Hz, 2H).

4-Amino-N-[2,3-diaza-spiro[4.4]non-3-en-2-yl)-ethylamino-methylene]-benzenesulfonamide (compound 4 from compound 2)

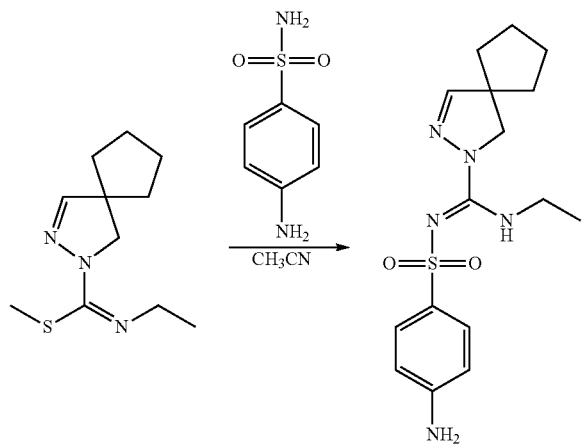

In a reactor equipped with a scrubber containing 50 mL 11% aqueous NaOCl, 5 mL 50% aqueous NaOH and 50 mL water, 4.00 g (1 mol equiv.) N-Ethyl-2,3-diaza-spiro[4.4]non-3-ene-2-carboximidothioic acid methyl ester and 3.06 g (1 mol equiv.) sulfanilamide were taken up in 175 mL of acetonitrile. The reaction mixture was refluxed for 18 h. and subsequently concentrated to approximately half the volume by distilling off acetonitrile at atmospheric pressure. After cooling to room temperature, 30 mL 2N NaOH and 100 mL DCM were added and the mixture was stirred for 5 minutes. The layers were separated and the organic phase was washed twice with water (precipitating solids during second wash collected with the organic phase). The organic phase was concentrated to approximately ⅓ of the volume under reduced pressure, and the solids were filtered off, washed twice with 5 mL of DCM and dried in vacuo at 50° C. to yield 3.14 g of a white solid. Another 0.99 g of solid material was obtained from the mother liquor upon standing overnight, bringing the total yield to 67%. $^1$H NMR (400 MHz, $CD_3CN$) δ 1.04 (t, J=7.5 Hz, 3H), 1.58-1.83 (m, 8H), 3.36-3.44 (m, 2H), 3.68 (br.s., 2H), 4.63 (br.s., 2H), 6.64 (d, J=8.7 Hz, 2H), 6.95 (s, 1H), 3.96 (br.s, 1H), 7.54 (d, J=8.7 Hz, 2H). HR-MS [M+H]$^+$350.1670; MS-MS [m/z] 257, 195, 178, 156 and 125 (identical to reference sample of compound 4 prepared by acidic deprotection of compound 3).

1H-Indole-5-sulfonic acid (2,3-diaza-spiro[4.4]non-3-en-2-yl)-ethylamino-methyleneamide (compound 38)

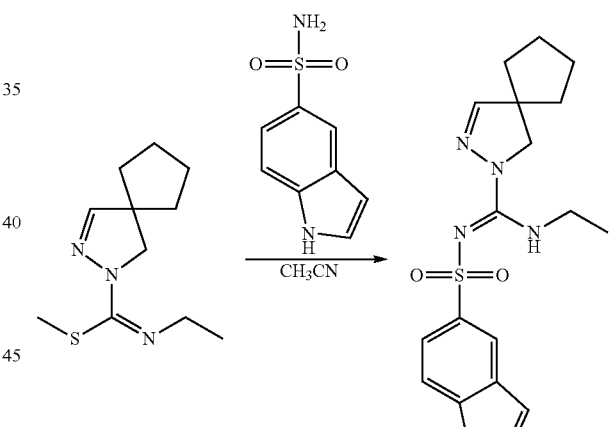

100 mg (1 mol equiv.) N-Ethyl-2,3-diaza-spiro[4.4]non-3-ene-2-carboximidothioic acid methyl ester and 92.5 mg (1.05 mol equiv.) 1H-indole-5-sulfonic acid amide were added to 3 mL acetonitrile. The reaction mixture was refluxed overnight and volatiles were removed under reduced pressure. The residue was taken up in ethyl acetate and extracted with 2N NaOH. The organic layer was dried over $Na_2SO_4$, filtered and evaporated to dryness. Purification by flash chromatography on silica gel ($Et_2O$:EtOAc=1:1) afforded 152 mg (87%) 1H-indole-5-sulfonic acid (2,3-diaza-spiro[4.4]non-3-en-2-yl)-ethylamino-methyleneamide. $^1$H NMR (400 MHz, $CDCl_3$) δ 1.14 (t, J=7.2 Hz, 3H), 1.59-1.79 (m, 8H), 3.43-3.51 (m, 2H), 3.79 (br.s., 2H), 6.63-6.65 (m, 1H), 6.76 (s, 1H), 6.99 (br.s., 1H), 7.30 (t, J=2.8 Hz, 1H), 7.43 (d, J=8.6 Hz, 1H), 7.76 (dd, J=8.6, 1.8 Hz, 1H), 8.27 (br.s., 1H), 8.54 (br.s., 1H).

| Comp | structure | TLC $R_f(x)$ | LCMS $R_t$ | m.p. °C. |
|---|---|---|---|---|
| | | | | Physico-chemical properties |
| 1 | 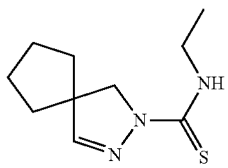 | 0.46 (a) | 1.95 | 120-121 |
| 2 | 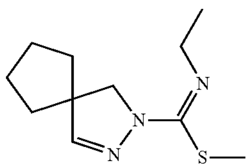 | 0.35 (b) | 0.97 | |
| 3 | 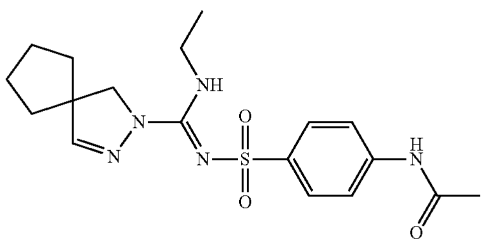 [SMILES: CCN/C(=N\S(=O)(=O)c1ccc(NC(C)=O)cc1)N1CC2(C=N1)CCCC2] | 0.38 (c) | 1.56 | |
| 4 | 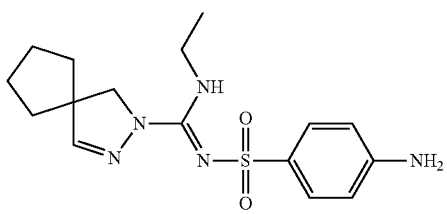 [SMILES: CCN/C(=N\S(=O)(=O)c1ccc(N)cc1)N1CC2(C=N1)CCCC2] | 0.28 (e) | 1.55 | 141-142 |
| 5 | 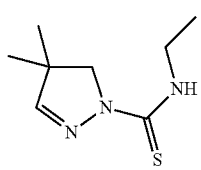 | 0.30 (a) | 1.73 | 66-67 |
| 6 | 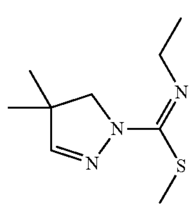 | 0.50 (b) | 0.89 | |
| 7 | 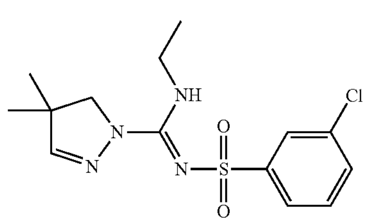 [SMILES: CCN/C(=N\S(=O)(=O)c1cccc(Cl)c1)N1CC(C)(C)C=N1] | 0.30 (b) | 1.97 | |

-continued

| Comp | structure | TLC $R_f(x)$ | LCMS $R_t$ | m.p. ° C. |
|---|---|---|---|---|
| 8 | 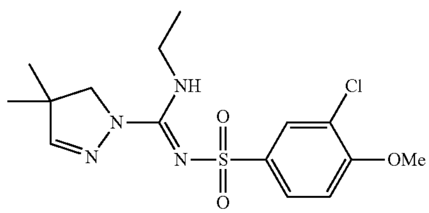 [SMILES: CCN/C(=N\S(=O)(=O)c1ccc(OC)c(Cl)c1)N1CC(C)(C)C=N1] | 0.30 (b) | 1.87 | |
| 9 | 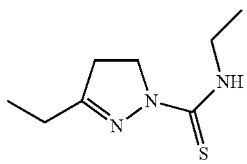 | 0.23 (a) | 1.66 | |
| 10 | 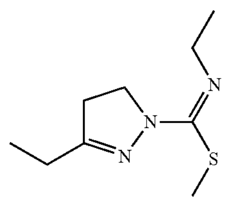 | 0.18 (b) | 0.95 | |
| 11 | 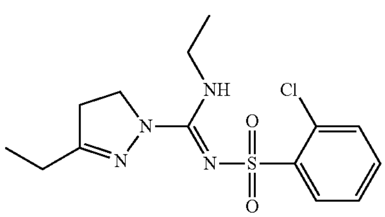 [SMILES: CCN/C(=N\S(=O)(=O)c1ccccc1Cl)N1CCC(CC)=N1] | 0.22 (b) | 1.76 | 87-88 |
| 12 | 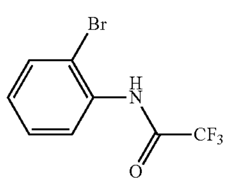 [SMILES: O=C(Nc1ccccc1Br)C(F)(F)F] | 0.51 (d) | 1.86 | 58-59 |
| 13 | 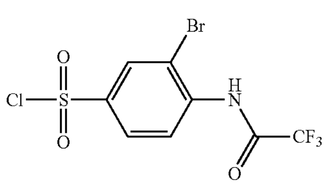 [SMILES: O=C(Nc1ccc(S(=O)(=O)Cl)cc1Br)C(F)(F)F] | 0.30 (d) | 2.15 | 60-61 |
| 14 | 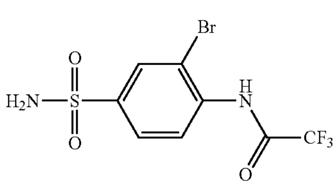 [SMILES: NS(=O)(=O)c1ccc(NC(=O)C(F)(F)F)c(Br)c1] | 0.51 (b) | 1.56 | 171-172 |

-continued

| Comp | structure | TLC $R_f(x)$ | LCMS $R_t$ | m.p. °C. |
|---|---|---|---|---|
| 15 | 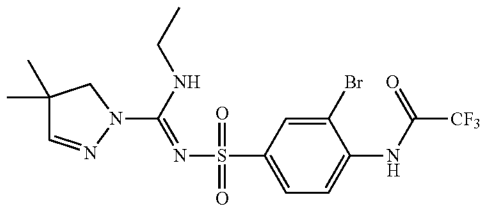 [SMILES: CCN/C(=N\S(=O)(=O)c1ccc(NC(=O)C(F)(F)F)c(Br)c1)N1CC(C)(C)C=N1] | 0.29 (b) | 1.92 | |
| 16 | 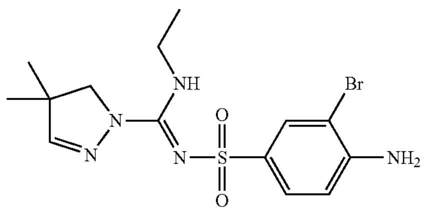 [SMILES: CCN/C(=N\S(=O)(=O)c1ccc(N)c(Br)c1)N1CC(C)(C)C=N1] | 0.18 (b) | 1.70 | |
| 17 | 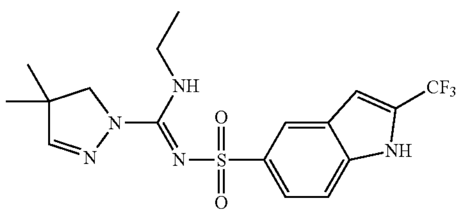 [SMILES: CCN/C(=N\S(=O)(=O)c1ccc2[nH]c(C(F)(F)F)cc2c1)N1CC(C)(C)C=N1] | 0.25 (b) | 1.80 | |
| 18 | 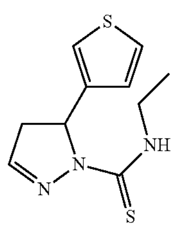 | 0.64 (b) | 1.64 | |
| 19 | 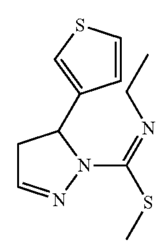 [SMILES: CC/N=C(/SC)N1N=CCC1c1ccsc1] | 0.30 (b) | 0.98 | |
| 20 | 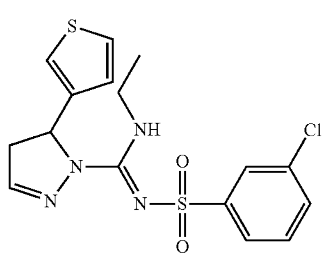 [SMILES: CCN/C(=N\S(=O)(=O)c1cccc(Cl)c1)N1N=CCC1c1ccsc1] | 0.29 (b) | 1.77 | |

-continued

|  |  | Physico-chemical properties | | |
|---|---|---|---|---|
| Comp | structure | TLC $R_f(x)$ | LCMS $R_t$ | m.p. °C. |
| 21 | (structure) | 0.28 (b) | 1.19 | 184-185 |
| 22 | (structure) | 0.30 (b) | 1.26 |  |
| 23 | (structure) | 0.04 (b) | 0.81 |  |
| 24 | (structure) | 0.20 (c) | 1.27 |  |
| 25 | (structure) | 0.34 (a) | 1.73 |  |
| 26 | (structure) | 0.32 (b) | 0.83 |  |
| 27 | (structure) | 0.40 (b) | 1.86 |  |
| 28 | (structure) | 0.08 (a) | 1.39 | 141-142 |

-continued

| Comp | structure | TLC R$_f$(x) | LCMS R$_t$ | m.p. °C. |
|---|---|---|---|---|
| 29 | 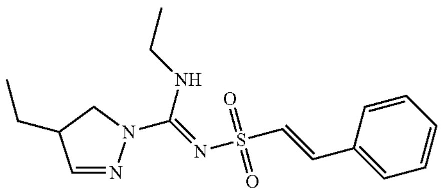 [SMILES: CCN/C(=N\S(=O)(=O)/C=C/c1ccccc1)N1CC(CC)C=N1] | 0.25 (b) | 1.86 | 91-92 |
| 30 | 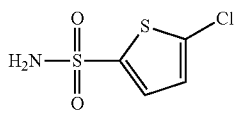 | 0.59 (b) | 1.36 | 109-110 |
| 31 | 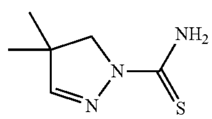 | 0.44 (b) | 1.22 | 149-150 |
| 32 | 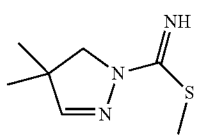 | 0.14 (b) | 0.83 | |
| 33 | 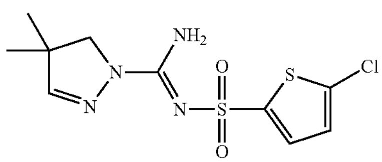 [SMILES: CC1(C)C=NN(/C(N)=N/S(=O)(=O)c2ccc(Cl)s2)C1] | 0.32 (b) | 1.81 | 164-165 |
| 34 | 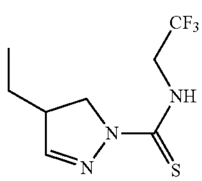 | 0.34 | 1.91 | |
| 35 | 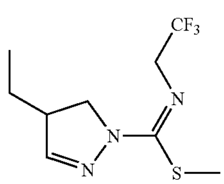 [SMILES: CCC1C=NN(/C(=N\CC(F)(F)F)SC)C1] | 0.63 (a) | 0.94 | |
| 36 | 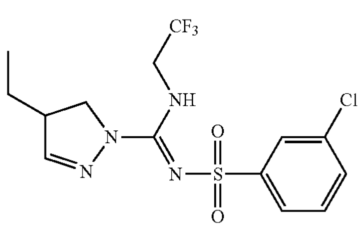 [SMILES: CCC1C=NN(/C(=N/S(=O)(=O)c2cccc(Cl)c2)NCC(F)(F)F)C1] | 0.30 (b) | 2.02 | |

Physico-chemical properties

| Comp | structure | Physico-chemical properties | | |
|---|---|---|---|---|
| | | TLC $R_f(x)$ | LCMS $R_t$ | m.p. °C. |
| 37 | 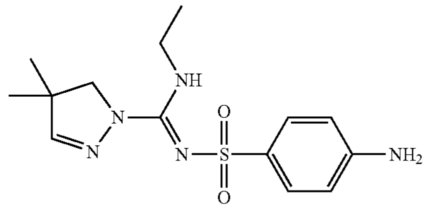 [SMILES: CCN/C(=N\S(=O)(=O)c1ccc(N)cc1)N1CC(C)(C)C=N1] | 0.45 (d) | 1.39 | |
| 38 | 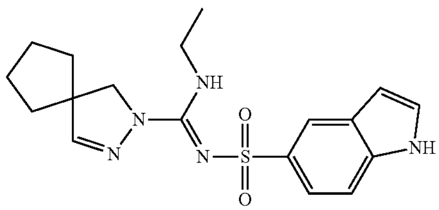 [SMILES: CCN/C(=N\S(=O)(=O)c1ccc2[nH]ccc2c1)N1CC2(C=N1)CCCC2] | 0.20 (b) | 1.72 | |

$R_f$ (x) = $R_f$-value, (x) between brackets: TLC mobile phase: (a) = diethylether:PA = 1:1; (b) = ether; (c) EA; (d) = diethylether:PA = 1:3; (e) = DCM:MeOH = 98:4; $R_t$ = retention time (in minutes) in LC-MS analysis

The invention claimed is:

1. A process for the preparation of a compound of formula (I):

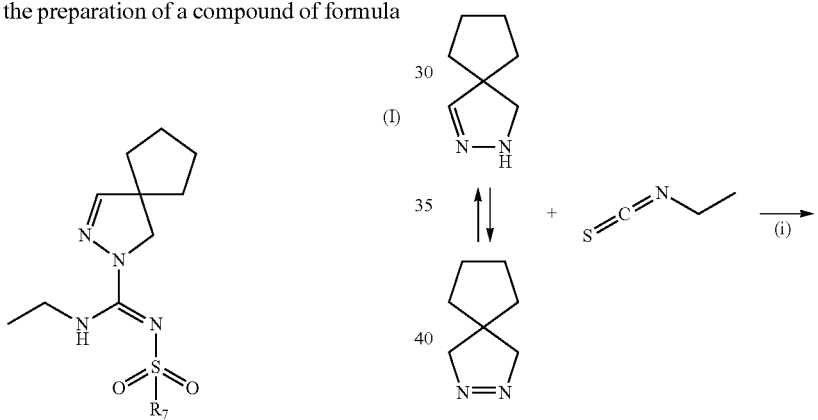

or a tautomer, stereoisomer, or a pharmacologically acceptable salt thereof, wherein:

$R_7$ represents a monocyclic, or a fused-bicyclic aromatic or hetero-aromatic group, which groups are unsubstituted or substituted with one to five substituents which can be the same or different, selected from the group consisting of halogen, trifluoromethyl, trifluoromethoxy, cyano, $C_{1-3}$-alkyl, $C_{1-3}$-alkoxy, hydroxy, amino, acetyl, acetamido, trifluoroacetamido, —$CONH_2$, —$SO_2NH_2$ and —$CO_2H$ or $R_7$ represents a 2-aryl-ethenyl group or a 2-aryl-ethynyl group, or $R_7$ represents a piperidinyl group unsubstituted or substituted with one to four fluoro atoms or a $CF_3$ group, or $R_7$ represents a 2,3-dihydroindolyl group or a benzimidazol-2-one group comprising the steps of:

(i) reacting 2,3-diaza-spiro[4.4]non-2-ene or 2,3-diaza-spiro[4.4]non-1-ene, or salts thereof with ethyl isothiocyanate, to yield 2,3-diazaspiro[4.4]non-3-ene-2-carbothioic acid ethylamide or its tautomer;

(ii) reacting the latter with iodomethane or methyl p-toluenesulfonate yielding N-ethyl-2,3-diaza-spiro[4.4]non-3-ene-2-carboximido-thioic acid methyl ester,

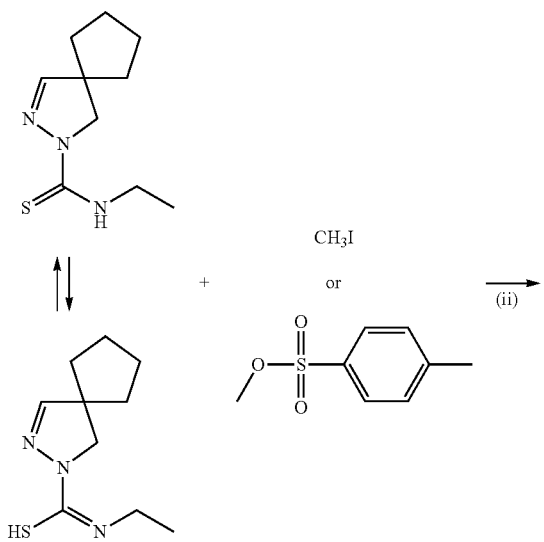

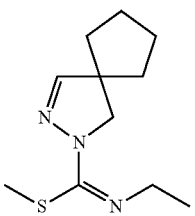

(iii) reacting the obtained N-ethyl-2,3-diaza-spiro[4.4]non-3-ene-2-carboximido-thioic acid methyl ester with a sulfonamide compound of formula $R_7SO_2NH_2$, wherein $R_7$ has the meaning given above, to give a compound of formula (I):

(I)

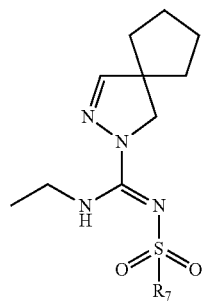

(iv) isolating the compound of formula (I) from the reaction mixture.

2. A process as claimed in claim 1, for the preparation of a compound of formula (I), wherein:
- $R_7$ represents a monocyclic, or a fused-bicyclic aromatic or hetero-aromatic group, which groups are unsubstituted or substituted with one to five substituents which can be the same or different, selected from the group consisting of halogen, trifluoromethyl, trifluoromethoxy, cyano, $C_{1-3}$-alkyl, $C_{1-3}$-alkoxy, hydroxy, amino, acetyl, acetamido, trifluoroacetamido, —$CONH_2$, —$SO_2NH_2$ and —$CO_2H$ or $R_7$ represents a 2-aryl-ethenyl group or a 2-aryl-ethynyl group, or
- $R_7$ represents a piperidinyl group, or
- $R_7$ represents a 2,3-dihydroindolyl group or a benzimidazol-2-one group.

3. A process as claimed in claim 1 wherein $R_7$ represents a monocyclic, or a fused-bicyclic aromatic or hetero-aromatic group, which groups are unsubstituted or substituted with one or two substituents chosen from methyl, methoxy, fluoro, chloro, bromo, cyano, acetamido, trifluoroacetamido, trifluoromethyl, amino or hydroxy.

4. A process as claimed in claim 1, for the preparation of a compound of formula

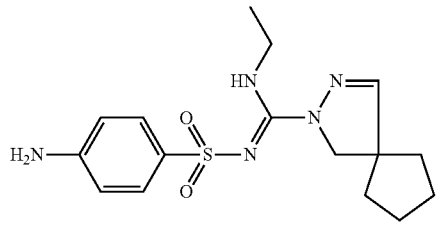 [SMILES: CCN/C(=N\S(=O)(=O)c1ccc(N)cc1)N1CC2(C=N1)CCCC2]

and tautomers and salt forms thereof,
comprising the steps of:
(i) reacting 2,3-diaza-spiro[4.4]non-2-ene or 2,3-diaza-spiro[4.4]non-1-ene, or salts thereof, with ethyl isothiocyanate, to yield 2,3-diazaspiro[4.4]non-3-ene-2-carbothioic acid ethylamide or its tautomer (ii) reacting the latter with iodomethane or methyl p-toluenesulfonate yielding N-ethyl-2,3-diaza-spiro[4.4]non-3-ene-2-carboximido-thioic acid methyl ester,

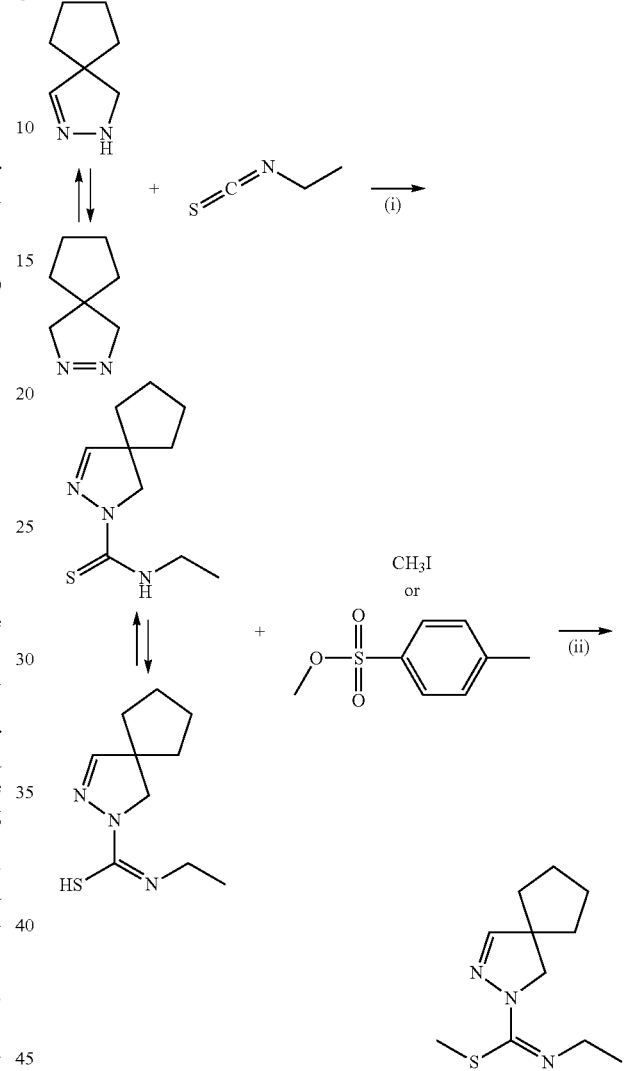

(iii) reacting the latter, as free base or salt thereof, with 4-acetamidobenzenesulfonamide yielding N-(4-{[(2,3-diaza-spiro[4.4]non-3-en-2-yl)-ethylamino-methylene]-sulfamoyl}-phenyl)-acetamide (iv) deprotecting the latter under acidic conditions, yielding 4-amino-N-[(2,3-diaza-spiro[4.4]non-3-en-2-yl)-ethylamino-methylene]-benzenesulfonamide

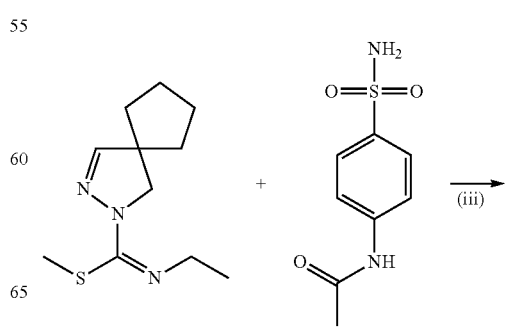

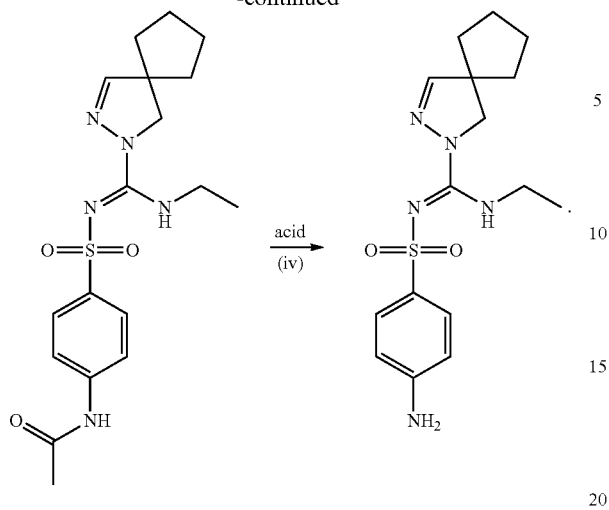
5. A process as claimed in claim 4, wherein step (iii) consists of reacting N-ethyl-2,3-diaza-spiro[4.4]non-3-ene-2-carboximidothioic acid methyl ester with sulfanilamide yielding 4-amino-N-[(2,3-diaza-spiro[4.4]non-3-en-2-yl)-ethylamino-methylene]-benzenesulfonamide:
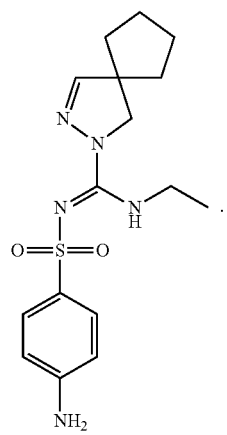
6. A compound selected from those of the formulae:
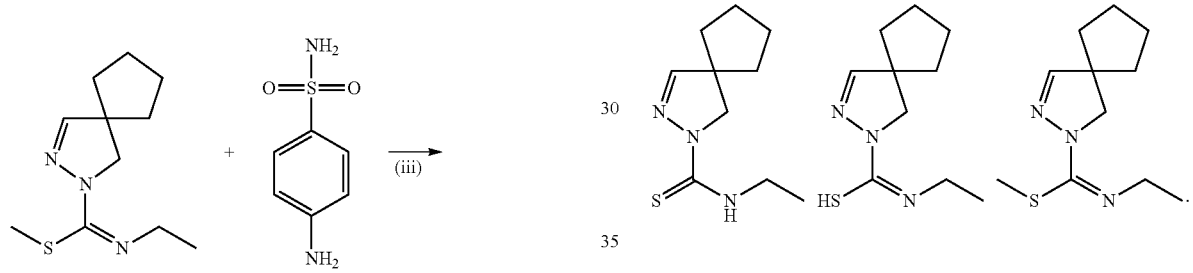
* * * * *